United States Patent
Liechti et al.

(10) Patent No.: US 11,959,929 B2
(45) Date of Patent: Apr. 16, 2024

(54) METHOD OF QUANTIFYING LYSERGIC ACID DIETHYLAMIDE (LSD) AND 2,3-DIHYDRO-3-HYDROXY-2-OXO LYSERGIDE (O-H-LSD) IN HUMAN PLASMA

(71) Applicant: Universitatsspital Basel, Basel (CH)

(72) Inventors: Matthias E. Liechti, Oberwil (CH); Urs Philipp Duthaler, Basel (CH)

(73) Assignee: Universitätsspital Basel, Basel (CH)

( * ) Notice: Subject to any disclaimer, the term of this patent is extended or adjusted under 35 U.S.C. 154(b) by 201 days.

(21) Appl. No.: 17/506,119

(22) Filed: Oct. 20, 2021

(65) Prior Publication Data

US 2022/0128580 A1    Apr. 28, 2022

Related U.S. Application Data

(60) Provisional application No. 63/105,266, filed on Oct. 24, 2020.

(51) Int. Cl.
*G01N 33/94* (2006.01)
*A61K 31/48* (2006.01)
*G01N 30/72* (2006.01)
*G01N 33/487* (2006.01)

(52) U.S. Cl.
CPC ............ *G01N 33/94* (2013.01); *A61K 31/48* (2013.01); *G01N 30/7206* (2013.01); *G01N 30/7233* (2013.01); *G01N 33/48714* (2013.01); *G01N 2500/00* (2013.01)

(58) Field of Classification Search
CPC ............ G01N 33/94; G01N 30/7206; G01N 30/7233; G01N 33/48714; G01N 2500/00; G01N 2800/30; G01N 2800/52; G01N 33/6893; A61K 31/48
See application file for complete search history.

(56) References Cited

PUBLICATIONS

Routledge, Philip et al. (2013). "Therapeutic Drug Monitoring (TDM)." Immunoassay Handbook (4th Edition)—9.22.1.2 Nonisotopic Immunoassay. Elsevier. Retrieved from <https://app.knovel.com/hotlink/pdf/id:kt00BK7OY1/immunoassay-handbook/nonisotopic-immunoassay>. (Year: 2013).*

(Continued)

*Primary Examiner* — Jill A Warden
*Assistant Examiner* — Michael Paul Shimek
(74) *Attorney, Agent, or Firm* — Kohn and Associates PLLC

(57) ABSTRACT

A method of measuring and identifying LSD and its major metabolite O-H-LSD, by obtaining a sample from an individual, and measuring, identifying, and quantifying LSD and O-H-LSD in the sample by performing a LC-MS/MS analysis. A method of treating and monitoring individuals taking LSD, by administering a microdose of LSD, a prodrug of LSD, or an analog of LSD to the individual, monitoring the individual by obtaining a sample from an individual and measuring and identifying the analytes in the sample by performing a LC-MS/MS analysis, and adjusting the microdose based on the amount of LSD quantified in the LC-MS/MS analysis. A method of adjusting dosing of LSD, by administering a microdose of LSD, a prodrug of LSD, or an analog of LSD to the individual, and adjusting the microdose based on blood concentration analytics.

5 Claims, 7 Drawing Sheets

(56) References Cited

PUBLICATIONS

Bershad, Anya K., et al. "Preliminary report on the effects of a low dose of LSD on resting-state amygdala functional connectivity." Biological Psychiatry: Cognitive Neuroscience and Neuroimaging 5.4 (2020): 461-467. (Year: 2020).*

Luethi, Dino, et al. "Cytochrome P450 enzymes contribute to the metabolism of LSD to nor-LSD and 2-oxo-3-hydroxy-LSD: Implications for clinical LSD use." Biochemical pharmacology 164 (2019): 129-138. (Year: 2019).*

Berg T, Jørgenrud B, & Strand DH (2013). Determination of buprenorphine, fentanyl and LSD in whole blood by UPLC-MS-MS. Journal of Analytical Toxicology 37: 159-165.

Bershad AK, Schepers ST, Bremmer MP, Lee R, & de Wit H (2019). Acute Subjective and Behavioral Effects of Microdoses of Lysergic Acid Diethylamide in Healthy Human Volunteers. Biological Psychiatry 86: 792-800.

Bogusz MJ, Maier RD, Kruger KD, & Kohls U (1998). Determination of common drugs of abuse in body fluids using one isolation procedure and liquid chromatography-atmospheric-pressure chemical-ionization mass spectrometry. Journal of Analytical Toxicology 22: 549-558.

Burnley BT, & George S (2003). The development and application of a gas chromatography-mass spectrometric (GC-MS) assay to determine the presence of 2-oxo-3-hydroxy-LSD in urine. Journal of Analytical Toxicology 27: 249-252.

Cai J, & Henion J (1996). On-line immunoaffinity extraction-coupled column capillary liquid chromatography/tandem mass spectrometry: Trace analysis of LSD analogs and metabolites in human urine. Analytical Chemistry 68: 72-78.

Canezin J, Cailleux A, Turcant A, Le Bouil A, Harry P, & Allain P (2001). Determination of LSD and its metabolites in human biological fluids by high-performance liquid chromatography with electrospray tandem mass spectrometry. Journal of Chromatography B: Biomedical Sciences and Applications 765: 15-27.

Caspar AT, Kollas AB, Maurer HH, & Meyer MR (2018). Development of a quantitative approach in blood plasma for low-dosed hallucinogens and opioids using LC-high resolution mass spectrometry. Talanta 176: 635-645.

Chung A, Hudson J, & McKay G (2009). Validated ultra-performance liquid chromatography-tandem mass spectrometry method for analyzing LSD, iso-LSD, nor-LSD, and O-H-LSD in blood and urine. Journal of Analytical Toxicology 33: 253-259.

Cui M, McCooeye MA, Fraser C, & Mester Z (2005). Quantitation of lysergic acid diethylamide in urine using atmospheric pressure matrix-assisted laser desorption/ionization ion trap mass spectrometry. Analytical Chemistry 76: 7143-7148.

Dolder PC, Liechti ME, & Rentsch KM (2014). Development and validation of a rapid turboflow LC-MS/MS method for the quantification of LSD and 2-oxo-3-hydroxy LSD in serum and urine samples of emergency toxicological cases. Analytical and Bioanalytical Chemistry 407: 1577-1584.

Dolder PC, Liechti ME, & Rentsch KM (2018). Development and validation of an LC-MS/MS method to quantify lysergic acid diethylamide (LSD), iso-LSD, 2-oxo-3-hydroxy-LSD, and nor-LSD and identify novel metabolites in plasma samples in a controlled clinical trial. Journal of Clinical Laboratory Analysis 32: 12-15.

Dolder PC, Schmid Y, Haschke M, Rentsch KM, & Liechti ME (2015). Pharmacokinetics and concentration-effect relationship of oral LSD in humans. Int J Neuropsychopharmacol 19: pyv072.

Dolder PC, Schmid Y, Steuer AE, Kraemer T, Rentsch KM, Hammann F, & Liechti ME (2017). Pharmacokinetics and pharmacodynamics of lysergic acid diethylamide in healthy subjects. Clinical Pharmacokinetics 56: 1219-1230.

EMA (2011). Guideline on bioanalytical method validation. European Medicines Agency (https://www.ema.europa.eu/en/bioanalytical-method-validation).

Family N, Maillet EL, Williams LTJ, Krediet E, Carhart-Harris RL, Williams TM, Nichols CD, Goble DJ, & Raz S (2020). Safety, tolerability, pharmacokinetics, and pharmacodynamics of low dose lysergic acid diethylamide (LSD) in healthy older volunteers. Psychopharmacology 237: 841-853.

Favretto D, Frison G, Maietti S, & Ferrara SD (2007). LC-ESI-MS/MS on an ion trap for the determination of LSD, iso-LSD, nor-LSD and 2-oxo-3-hydroxy-LSD in blood, urine and vitreous humor. International Journal of Legal Medicine 121: 259-265.

FDA (2018). Bioanalytical Method Validation Guidance for Industry. U.S. Food and drug administration(https://www.fda.gov/regulatory-information/search-fda-guidance-documents/bioanalytical-method-validation-guidance-industry).

Fisichella M, Odoardi S, & Strano-Rossi S (2015). High-throughput dispersive liquid/liquid microextraction (DLLME) method for the rapid determination of drugs of abuse, benzodiazepines and other psychotropic medications in blood samples by liquid chromatography-tandem mass spectrometry (LC-MS/MS) and app. Microchemical Journal 123: 33-41.

Francom P, Andrenyak D, Lim HK, Bridges RR, Jones RT, & Foltz RL (1988). Determination of lsd in urine by capillary column gas chromatography and electron impact mass spectrometry. Journal of Analytical Toxicology 12: 1-8.

Gasser P, Holstein D, Michel Y, Doblin R, Yazar-Klosinski B, Passie T, & Brenneisen R (2014). Safety and efficacy of lysergic acid diethylamide-assisted psychotherapy for anxiety associated with life-threatening diseases. Journal of Nervous and Mental Disease 202: 513-520.

Grumann C, Henkel K, Stratford A, Hermanns-Clausen M, Passie T, Brandt SD, & Auwärter V (2019). Validation of an LC-MS/MS method for the quantitative analysis of 1P-LSD and its tentative metabolite LSD in fortified urine and serum samples including stability tests for 1P-LSD under different storage conditions. Journal of Pharmaceutical and Biomedical Analysis 174: 270-276.

Hoja H, Marquet P, Verneuil B, Lotfi H, Dupuy JL, & Lachâtre G (1997). Determination of LSD and N-demethyl-LSD in urine by liquid chromatography coupled to electrospray ionization mass spectrometry. Journal of Chromatography B: Biomedical Applications 692: 329-335.

Holze F, Duthaler U, Vizeli P, Muller F, Borgwardt S, & Liechti ME (2019). Pharmacokinetics and subjective effects of a novel oral LSD formulation in healthy subjects. British Journal of Clinical Pharmacology 85: 1474-1483.

Holze F, Liechti ME, Hutten N, Mason NL, Dolder PC, Theunissen EL, Duthaler U, Feilding A, Ramaekers JG, & Kuypers KPC (2021a). Pharmacokinetics and pharmacodynamics of lysergic acid diethylamide microdoses in healthy participants. Clinical and Pharmacological Therapeutics 109: 658-666.

Holze F, Vizeli P, Ley L, Müller F, Dolder P, Stocker M, Duthaler U, Varghese N, Eckert A, Borgwardt S, & Liechti ME (2021b). Acute dose-dependent effects of lysergic acid diethylamide in a double-blind placebo-controlled study in healthy subjects. Neuropsychopharmacology46: 537-544.

Horn CK, Klette KL, & Stout PR (2003). LC-MS analysis of 2-oxo-3-hydroxy LSD from urine using a Speedisk® positive-pressure processor with Cerex® Polychrom™ CLIN II columns. Journal of Analytical Toxicology 27: 459-463.

Hutten N, Mason NL, Dolder P, Theunissen EL, Holze F, Liechti ME, Varghese N, Eckert A, Feilding A, Ramaekers JG, & Kuypers KP (2020). Low dose LSD acutely increases BDNF blood plasma levels in healthy volunteers. ACS Pharmacologial Translational Science 31:461-466.

Hutten N, Mason NL, Dolder PC, & Kuypers KPC (2019). Motives and Side-Effects of Microdosing With Psychedelics Among Users. Internatonal Journal of Neuropsychopharmacology 22: 426-434.

Jang M, Kim J, Han I, & Yang W (2015). Simultaneous determination of LSD and 2-oxo-3-hydroxy LSD in hair and urine by LC-MS/MS and its application to forensic cases. Journal of Pharmaceutical and Biomedical Analysis 115: 138-143.

Johansen SS, & Jensen JL (2005). Liquid chromatography-tandem mass spectrometry determination of LSD, ISO-LSD and the main metabolite 2-oxo-3-hydroxy-LSD in forensic samples and application in a forensic case. Journal of Chromatography B: Analytical Technologies in the Biomedical and Life Sciences 825: 21-28.

(56) References Cited

PUBLICATIONS

Klette KL, Horn CK, Stout PR, & Anderson CJ (2002). LC-MS analysis of human urine specimens for 2-Oxo-3-hydroxy LSD: Method validation for potential interferants and stability study of 2-Oxo-3-hydroxy LSD under various storage conditions. Journal of Analytical Toxicology 26: 193-200.
Krebs TS, & Johansen PO (2013). Over 30 million psychedelic users in the United States. F1000Res 2: 98.
Kuypers KP, Ng L, Erritzoe D, Knudsen GM, Nichols CD, Nichols DE, Pani L, Soula A, & Nutt D (2019). Microdosing psychedelics: more questions than answers? An overview and suggestions for future research. Journal of Psychopharmacology 33: 1039-1057.
Kuypers KPC (2020). The therapeutic potential of microdosing psychedelics in depression. Therapeutic Advances in Psychopharmacology 10: 2045125320950567.
Libong D, Bouchonnet S, & Ricordel I (2003). A selective and sensitive method for quantitation of lysergic acid diethylamide (LSD) in whole blood by gas chromatography-ion trap tandem mass spectrometry. Journal of Analytical Toxicology 27: 24-29.
Liechti ME (2017). Modern Clinical Research on LSD. Neuropsychopharmacology 42: 2114-2127.
Lim HK, Andrenyak D, Francom P, Foltz RL, & Jones RT (1988). Quantification of LSD and N-Demethyl-LSD in Urine by Gas Chromatography/Resonance Electron Capture Ionization Mass Spectrometry. Analytical Chemistry 60: 1420-1425.
Martin R, Scharenkamp J, Gasse A, Pfeiffer H, & Kohler H (2013). Determination of psilocin, bufotenine, LSD and its metabolites in serum, plasma and urine by SPE-LC-MS/MS. International Journal of Legal Medicine 127: 593-601.
Nelson CC, & Foltz RL (1992). Determination of Lysergic Acid Diethylamide (LSD), Iso-LSD, and /V-Demethyl-LSD in Body Fluids by Gas Chromatography/ Tandem Mass Spectrometry. Analytical Chemistry 64: 1578-1585.
Musshoff, F. and T. Daldrup (1997). "Gas chromatographic/mass spectrometric determination of lysergic acid diethylamide (LSD) in serum samples." Forensic Science International 88: 133-140.
Papac DI, & Foltz RL (1990). Measurement of lysergic acid diethylamide (lsd) in human plasma by gas chromatography/ negative ion chemical ionization mass spectrometry. Journal of Analytical Toxicology 14: 189-190.
Paul BD, Mitchell JM, Burbage R, Moy M, & Sroka R (1990). Gas chromatographic-electron-impact mass fragmentometric determination of lysergic acid diethylamide in urine. Journal of Chromatography B: Biomedical Sciences and Applications 529: 103-112.
Paulke A, Kremer C, Wunder C, & Toennes SW (2012). Analysis of lysergic acid amide in human serum and urine after ingestion of Argyreia nervosa seeds. Analytical and Bioanalytical Chemistry 404: 531-538.

Pietsch J, Schulz K, Körner B, Trauer H, Dreßler J, & Gey M (2004). Alternative method for forensic determination of lysergic acid diethylamide and related compounds in body fluids by liquid-liquid extraction and HPLC with fluorescence detection. Chromatographia 60: 89-92.
Poch GK, Klette KL, & Anderson C (2000). The quantitation of 2-oxo-3-hydroxy lysergic acid diethylamide (O—H—LSD) in human urine specimens, a metabolite of LSD: Comparative analysis using liquid chromatography-selected ion monitoring mass spectrometry and liquid chromatography-ion trap mass spec. Journal of Analytical Toxicology 24: 170-179.
Ramaekers JG, Hutten N, Mason NL, Dolder P, Theunissen EL, Holze F, Liechti ME, Feilding A, & Kuypers KP (2021). A low dose of lysergic acid diethylamide decreases pain perception in healthy volunteers. Journal of Psychopharmacology 35:398-405.
Reuschel SA, Percey SE, Liu S, Eades DM, & Foltz RL (1999). Quantitative determination of LSD and a major metabolite, 2-oxo-3-hydroxy-LSD, in human urine by solid-phase extraction and gas chromatography-tandem mass spectrometry. Journal of Analytical Toxicology 23: 306-312.
Rule GS, & Henion JD (1992). Determination of drugs from urine by on-line immunoaffinity chromatography-high-performance liquid chromatography-mass spectrometry. Journal of Chromatography B: Biomedical Sciences and Applications 582: 103-112.
Sklerov JH, Kalasinsky KS, & Ehorn CA (1999). Detection of lysergic acid diethylamide (LSD) in urine by gas chromatography-ion trap tandem mass spectrometry. Journal of Analytical Toxicology 23: 474-478.
Sklerov JH, Magluilo J, Jr., Shannon KK, & Smith ML (2000). Liquid chromatography-electrospray ionization mass spectrometry for the detection of lysergide and a major metabolite 2-oxo-3-hydroxy-LSD, in urine and blood. Journal of Analytical Toxicology 24: 543-549.
Steuer AE, Poetzsch M, Stock L, Eisenbeiss L, Schmid Y, Liechti ME, & Kraemer T (2017). Development and validation of an ultra-fast and sensitive microflow liquid chromatography-tandem mass spectrometry (MFLC-MS/MS) method for quantification of LSD and its metabolites in plasma and application to a controlled LSD administration study in huma. Drug Testing and Analysis 9: 788-797.
White SA, Catterick T, Harrison ME, Johnston DE, Reed GD, & Webb KS (1997). Determination of lysergide in urine by high-performance liquid chromatography combined with electrospray ionisation mass spectrometry. Journal of Chromatography B: Biomedical Applications 689: 335-340.
Yanakieva S, Polychroni N, Family N, Williams LTJ, Luke DP, & Terhune DB (2019). The effects of microdose LSD on time perception: a randomised, double-blind, placebo-controlled trial. Psychopharmacology 236: 1159-1170.

* cited by examiner

FIGURE 1

| Publication | Analyte | Matrix | Methodology | Extraction steps | Mobile Phase | Run time min | Sample volume mL | rel. sensitivity pg/ml | abs. sensitivity pg | Quant range pg/ml |
|---|---|---|---|---|---|---|---|---|---|---|
| Present invention | LSD O-H-LSD | P | LC-MS/MS | PP | A: NH₄HCO₃ (pH 10) B: AcN/HCOOH (0.1%) | 4.0 | 0.05 | 10 | 0.5 | 10-10'000 |
| Berg et al., 2013 | LSD | B | LC-MS/MS | LLE + E/R | A: NH₄HCO₂ (pH 10.2) B: MeOH | ~7.5 | 0.5 | 36 | 18 | 130-10'000 |
| Bogusz et al., 1998 | LSD | S, B, U | LC-MS | SPE + E/R | Mixture of AcN and NH₄HCO₂ (pH 3) | N/A | 0.5-1.5 | 500 (LOD) | 250-750 | N/A |
| Burnley & George, 2003 | O-H-LSD | U | GC-MS | LLE, E/R + DRV | N/A | 10.8 | 5 | 1'000 | 5'000 | 500-50'000 |
| Cay & Henion, 1996 | LSD nor-LSD | U | LC-MS/MS | Online SPE | 30% AcN/30% MeOH/HOAc (0.1%)/ NH₄OAc | ~10 | 200 | 2.5 | 500 | N/A |
| Canezin et al., 2001 | LSD | P, B, U | LC-MS/MS | LLE + E/R | 40% H2O/60% AcN/0.1% HCOOH NH₄HCO₂ | ~8.0 | 1.0 | 20 | 20 | 10-4'000 |
| Caspar et al., 2018 | LSD | P | LC-HRM | LLE + E/R | A: NH₄HCO₂ (pH 3.4) B: MeOH:AcN (1:1) | 15 | 1.0 | 250 | 250 | 250-40'000 |
| Chung et al., 2009 | LSD O-H-LSD nor-LSD | B, U | LC-MS/MS | LLE + E/R | A: NH₄OAc (pH 4.0) B: AcN | 15 | 1.0 | 20 | 20 | 20-2'000 |
| Cui et al., 2005 | LSD | U | MALDI-MS | SPE | N/A | N/A | 1.0 | 1'000 | 1'000 | 1'000-100'000 |
| Dolder et al., 2018 | LSD O-H-LSD nor-LSD | P | LC-MS/MS | PP | A: NH₄OAc/HCOOH (0.1%) B: MeOH:AcN (1:1)/HCOOH (0.1%)/NH₄OAc C: AcN:Acetone:2-Propanol (1:1:1) | 15 | 0.1 | 50 | 5 | 50-10'000 |
| Dolder et al., 2015 | LSD O-H-LSD | P, U | LC-MS/MS | PP | A: NH₄OAc/HCOOH (0.1%) B: NH₄OAc/MeOH/HCOOH (0.5%) | 12.5 | 0.1 | 100 | 10 | 100-10'000 |
| Family et al., 2019 | LSD | P | LC-MS/MS | LLE + E/R | A: MeOH B: MeOH (10%)/HCOOH | N/A | 0.1 | 200 | 20 | 200-10'000 |

FIGURE 1 cont

| Publication | Analyte | Matrix | Methodology | Extraction steps | Mobile Phase | Run time min | Sample volume mL | rel. sensitivity pg/ml | abs. sensitivity pg | Quant range pg/ml |
|---|---|---|---|---|---|---|---|---|---|---|
| Present invention | LSD O-H-LSD | P | LC-MS/MS | PP | A: $NH_4HCO_3$ (pH 10) B: AcN/HCOOH (0.1%) | 4.0 | 0.05 | 10 | 0.5 | 10-10'000 |
| Favretto et al., 2007 | LSD O-H-LSD nor-LSD | B, U, V | LC-MS/MS | LLE + E/R | A: $NH_4HCO_2$ (pH 3)/HCOOH (0.1%) B: AcN/$NH_4HCO_2$/HCOOH (0.1%) | 12 | 2 | 20 | 40 | 20-10'000 |
| Fisichella et al., 2015 | LSD | B | LC-MS/MS | LLE + E/R | A: HCOOH (0.1%) B: MeOH/HCOOH (0.1%) | 13 | 0.5 | 2000 | 1000 | 2'000-100'000 |
| Francom et al., 1988 | LSD | U | GC-MS | LLE + E/R + DRV | Helium | ~16 | 5 | 500 | 2500 | 500-10'000 |
| Grumann et al., 2019 | LSD | U, S | LC-MS/MS | LLE + E/R | A: $H_2O$/AcN (1%)/HCOOH (0.1%)/$NH_4HCO_2$ B: AcN/$NH_4HCO_2$ | ~15 | 0.5 | 15 | 7.5 | 15-400 |
| Hoja et al., 1997 | LSD nor-LSD | U | LC-MS | SPE + E/R | AcN/$NH_4HCO_2$ (3:7) | ~13 | 2 | 50 | 100 | 50-20'000 |
| Horn et al., 2003 | O-H-LSD | U | LC-MS | SPE + E/R | A: $NH_4OAc$, Triethylamine (0.02%) B: AcN | 14 | 5 | 250 | 1250 | 250-30'000 |
| Jang et al., 2015 | LSD O-H-LSD | U, H | LC-MS/MS | LLE + E/R | A: $NH_4HCO_2$/HCOOH (0.2%) B: AcN/$NH_4HCO_2$/HCOOH (0.2%) | 10 | 0.1 | 25 | 2.5 | 25-10'000 |
| Johansen & Jensen, 2005 | LSD O-H-LSD | U, B | LC-MS/MS | LLE + E/R | A: AcN (5%)/HCOOH (0.05%) B: AcN/HCOOH (0.05%) | 20 | 1 | 10 | 10 | 10-50'000 |
| Klette et al., 2002 | O-H-LSD | U | LC-MS | LLE + SPE + E/R | $NH_4OAc$ (pH 8)/AcN | 21 | 5 | 500 | 2500 | 500-1250 |
| Libong et al., 2003 | LSD | B | GC-MS/MS | SPE + E/R | Helium | 20 | 2 | 20 | 40 | 20-10'000 |
| Lim et al., 1988 | LSD nor-LSD | U | GC-MS | LLE + E/R + DRV | Hydrogen | ~14.5 | 8 | 50 | 400 | 50-5'000 |
| Martin et al., 2013 | LSD O-H-LSD nor-LSD | P, S, U | LC-MS/MS | SPE + E/R | A: AcN/HCOOH (0.1%) B: $NH_4OAc$/HCOOH (0.1%) | 29 | 1 | 20 | 20 | 20-2'000 |
| Musshoff et al., 1997 | LSD | S | GC-MS | LLE + E/R + DRV | N/A | ~32 | 1 | 100 | 100 | 100-10'000 |

FIGURE 1 cont

| Publication | Analyte | Matrix | Methoddogy | Extraction steps | Mobile Phase | Run time min | Sample volume mL | rel. sensitivity pg/ml | abs. sensitivity pg | Quant range pg/ml |
|---|---|---|---|---|---|---|---|---|---|---|
| Present invention | LSD O-H-LSD | P | LC-MS/MS | PP | A: NH$_4$HCO$_3$ (pH 10) B: AcN/HCOOH (0.1%) | 4.0 | 0.05 | 10 | 0.5 | 10-10'000 |
| Nelson et al., 1992 | LSD nor-LSD | U, B | GC-MS/MS | LLE + E/R + DRV | Hydrogen | ~11 | 2-5 | 20 | 40-100 | 20-1'000 |
| Papac & Foltz, 1990 | LSD | P | GC-MS | LLE + E/R + DRV | Hydrogen | ~8 | 2 | 100 | 200 | 100-3'000 |
| Paul et al. 1990 | LSD | U | GC-MS | LLE/SPE + E/R + DRV | Helium | ~8 | 10 | 50 | 500 | 50-2'000 |
| Paulke et al. 2012 | LSD | S, U | LC-FLD | SPE + E/R | A: MeOH B: AcN C: NH$_4$HCO$_2$ (pH 6.8) | 25 | 1 | 170 | 170 | 250-17'800 |
| Pietsch et al. 2004 | LSD nor-LSD | S, U | LC-FLD | LLE + E/R | AcN:PBS (33:67) | ~12 | 1 | 200 | 200 | 200-2'500 |
| Poch et al. 2000 | O-H-LSD | U | LC-MS LC-MS/MS | SPE + E/R | A: NH$_4$OAc, Triethylamine (0.02%) B: AcN | 21 | 5 | 400 | 2000 | 400-8'000 |
| Reuschel et al., 1999 | LSD O-H-LSD | U | GC-MS/MS | SPE + E/R | Hydrogen | 7 | 4 | 10 | 400 | 10-5'000 |
| Rule et al. 1992 | LSD | U | LC-MS | online SPE | AcN/H$_2$O (pH 3 with HCOOH/NH$_4$OAc) | ~6 | ~4 | ~500 | ~2000 | N/A |
| Sklerov et al., 2000 | LSD O-H-LSD | B, U | LC-MS | LLE + E/R | A: NH$_4$HCO$_2$ (pH 4.3) B: MeOH | 15 | 1 | 100 | 100 | 100-6'000 |
| Sklerov et al., 1999 | LSD O-H-LSD | B, U | GC-MS/MS | SPE + E/R | Helium | ~10 | 5 | 80 | 400 | 80-2'000 |
| Steuer et al. 2016 | LSD O-H-LSD nor-LSD | P | LC-MS/MS | SPE + E/R | A: NH$_4$HCO$_2$ (pH 3.5) B: AcN/HCOOH (0.1%) | 3 | 0.5 | 10 | 5 | 10-20'000 |
| White et al., 1997 | LSD | P | LC-MS | SPE + E/R | NH$_4$OAc/Triethylamine/ AcN (pH 8.0) | ~18 | 5 | 500 | 2500 | 500-10'000 |

O-H-LSD

LSD

METHOD OF QUANTIFYING LYSERGIC ACID DIETHYLAMIDE (LSD) AND 2,3-DIHYDRO-3-HYDROXY-2-OXO LYSERGIDE (O-H-LSD) IN HUMAN PLASMA

GRANT INFORMATION

Research in this application was supported in part by a grant from the Swiss National Science Foundation (Grant No. 32003B_185111).

BACKGROUND OF THE INVENTION

1. Technical Field

The present invention relates to compositions and methods for quantification and identification of lysergic acid diethylamide (LSD) and its major metabolite 2,3-dihydro-3-hydroxy-2-oxo lysergide (O-H-LSD) in human plasma.

2. Background Art

LSD is a prototypical psychedelic (hallucinogen) that is widely used for recreational purposes (Krebs & Johansen, 2013). However, efforts are ongoing to use LSD among others for treatment of depression and anxiety, substance use, and cluster headache (Gasser et al., 2014; Liechti, 2017). In addition, LSD microdosing has recently become popular to improve cognitive function and mood. In this regard, users take very low doses of 5-20 μg LSD in 2- to 5-day intervals (Hutten et al., 2019). Furthermore, such microdoses may also be used therapeutically to treat medical conditions in the future (Kuypers et al., 2019; Kuypers, 2020). For example, microdoses of LSD reduce pain perception (Ramaekers et al., 2021) and increased markers of neuroregeneration in humans (Hutten et al., 2020).

With a rapidly growing interest of applying LSD as a potential therapeutic agent for various psychiatric disorders, it is essential to expand the knowledge of its clinical pharmacology and in particular its pharmacokinetics (PK). Therefore, measuring LSD exposure in patients and users is essential to research associations between drug exposure and therapeutic or toxic effects. PK data is needed to generate reference concentration values to adjust dosing in patients treated with LSD. For example, plasma concentrations may be measured in patients, who do not show the expected acute psychoactive response to LSD or an insufficient therapeutic response. To this aim, a method is needed to measure the LSD concentration in plasma at a defined time point or repeatedly ($C_{max}$ or full PK profile) and the patient's values can then be compared with reference data from a larger population to determine correct dosing and to adjust dosing within a therapeutic drug monitoring (TDM) approach for LSD-assisted therapy. Moreover, drug-drug interaction studies are pending, which are crucial to ensure safe and effective therapies. In this context, it is important to quantify metabolites of LSD as well, such as O-H-LSD, which assist interpreting drug-drug interaction data. Finally, suitable bioanalytical methods are required to identify drug abuse considering that the access to LSD, if available as therapeutic agent, might be easier.

PK data has been established mostly for higher doses of LSD (Dolder et al., 2015; Dolder et al., 2017; Holze et al., 2019; Holze et al., 2021b). In contrast, PK data on microdoses of LSD is scarce (Family et al., 2020; Holze et al., 2021a). A key limitation to establishing PK data on microdosing as a sensitive analytical method to detect and validly quantify LSD plasma levels after administration of very low doses of LSD. The present innovation provides for such a method.

Overall, detection and reliable quantitation of LSD is difficult, especially when microdoses are administered. Several studies investigated the subjective and behavioral effects of LSD microdoses (Bershad et al., 2019; Holze et al., 2021a; Yanakieva et al., 2019); however, only two studies managed to report also plasma concentration time profiles of LSD (Family et al., 2020; Holze et al., 2021). Because the sensitivity of the employed methodology was insufficient, plasma levels of 5 μg LSD doses could not be determined in one study (Family et al., 2020) and for 10 and 20 μg treatments only incomplete profiles were established, which did only partially cover invasion and elimination of LSD. In the other study, the method of quantification was sensitive and consisted of the method presented here, but plasma could only be sampled in a fraction of the participants (Holze et al., 2021). Therefore, more PK data on LSD including microdoses is needed and a sensitive and work-optimized novel method of detection is needed.

In the past decades, several methods have been developed to quantify LSD and O-H-LSD as summarized in FIG. 1. (Legend for FIG. 1: Analytes (LSD: lysergic acid diethylamide, O-H-LSD: 2,3-dihydro-3-hydroxy-2-oxo lysergide, nor-LSD: norlysergic acid diethylamide); Matrices (P: plasma, S: serum, B: whole blood, U: urine, H: hair, V: vitreous humor); Methodology (LC-MS/MS: liquid chromatography tandem mass spectrometry, LC-MS: liquid chromatography mass spectrometry, GC-MS: gas chromatography mass spectrometry, GC-MS/MS: gas chromatography tandem mass spectrometry, LC-FLD: High performance liquid chromatography fluoresence detection, MALDI-MS: Matrix-assisted laser desorption ionisation mass spectrometry, LC-HRM: Liquid chromatography high resolution mass spectrometry); Extraction (PP: Plasma protein precipitation extraction, LLE: Liquid-liquid extraction, SPE: Solid-phase extraction, online SPE: automated SPE, E/R: Sample evaporation and reconstitution, DRV: derivatization); Mobile Phase ($H_2O$: Water, AcN: Acetonitrile, MeOH: Methanol, $NH_4OAc$: Ammonium acetate, $NH_4HCO_3$: Ammonium bicarbonate, $NH_4HCO_2$: Ammonium formate, HCOOH: formic acid, HOAc: Acetic acid); Rel. sensitivity (Relative sensitivity of the method (pg/ml)); Abs. sensitivity (Absolute sensitivity of the method (pg). Rel. sensitivity multiplied by the sample volume (ml)), and Quant range (Quantification range corresponding to the limits of quantification).) Most methods have focused on quantification of LSD for drug screening or preliminary pharmacokinetic studies involving limited sample size. In the 1990s, several gas chromatography single mass spectrometry methods were developed for quantification of LSD and O-H-LSD mainly in urine but also blood plasma. Those methods required large sample volumes of 2-10 ml and to that effect a laborious extraction procedure involving liquid-liquid extraction or solid-phase extraction. The originated extract had to be evaporated and resuspended in a solvent, which is suitable for gas chromatographic analysis. Finally, in most cases derivatization of the analytes was necessary to improve the separation and sensitivity of the methods. Around the turn of the millennium, the first liquid chromatography single and tandem mass spectrometry (LC-MS/MS) methods were established for LSD analysis in human body fluids. Those methods required less sample (~1 ml) but still a complex extraction protocol, which involved either liquid-liquid or solid phase purification of the biological sample. However, in contrast to gas chromatography methods, derivatization could be omitted. Importantly, total analysis time per sample was rarely below 10 minutes. In the last decade, novel LC-MS/MS methods evolved, achieving lower limits of quantification in the low pg/ml range. Strikingly, only few methods achieved a lower limit of quantification suitable for analyzing the PK of LSD microdoses. Those methods made use of elaborative sample processing methods, as described above, and thus required still a moderate amount of sample (~0.5 ml). Overall and to our best knowledge, none of the published methods are suitable for high-throughput analysis and for that reason not eligible when large amounts of samples must be analyzed. In addition, these methods are, because of their complex extraction procedure, not practical for routine therapeutic drug monitoring (TDM) analysis.

Therefore, there remains a need for a novel and an effective method of evaluating LSD and O-H-LSD in plasma especially following treatment with LSD microdoses.

SUMMARY OF THE INVENTION

The present invention provides for a method of measuring and identifying LSD and its major metabolite O-H-LSD, by obtaining a sample from an individual, and measuring, identifying, and quantifying LSD and O-H-LSD in the sample by performing a LC-MS/MS analysis.

The present invention provides for a method of treating and monitoring individuals taking LSD, by administering a microdose of LSD, a prodrug of LSD, or an analog of LSD to the individual, monitoring the individual by obtaining a sample from an individual and measuring and identifying the analytes in the sample by performing a LC-MS/MS analysis, and adjusting the microdose based on the amount of LSD quantified in the LC-MS/MS analysis.

The present invention also provides for a method of adjusting dosing of LSD, by administering a microdose of LSD, a prodrug of LSD, or an analog of LSD to the individual, and adjusting the microdose based on blood concentration analytics.

DESCRIPTION OF THE DRAWINGS

Other advantages of the present invention are readily appreciated as the same becomes better understood by reference to the following detailed description when considered in connection with the accompanying drawings wherein:

FIG. 1 is a table comparing the present invention with previously published analytical methods that quantify LSD in human body fluids or tissues;

DETAILED DESCRIPTION OF THE INVENTION

Figure 2:
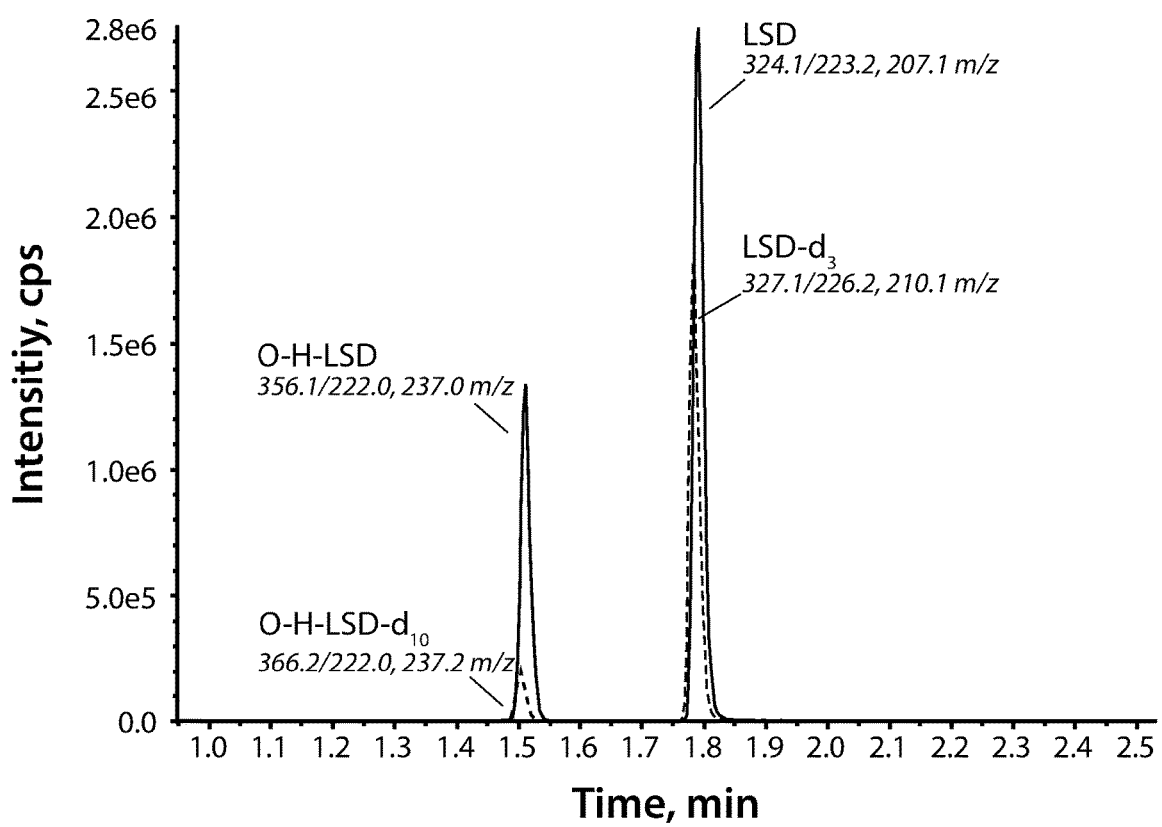
FIG. 2 is a graph of the chromatographic separation of LSD and O-H-LSD and their respective internal standards, LSD-$d_3$ and O-H-LSD-$d_{10}$, in human plasma.

The present invention provides for a method of measuring LSD and its metabolite O-H-LSD in a human sample such as plasma. This method is validated providing information of the quality and performance of the method and an application in human subjects including first description of the pharmacokinetics of very low doses of LSD including 5-25 µg LSD microdoses.

"Sample" as used herein, refers to a sample of plasma, blood, urine, saliva, or other bodily fluid from an individual, and preferably from a human or mammal.

"Metabolite" as used herein, refers to an intermediate or end product of an original active compound as the product of metabolism. The metabolites in the present invention are preferably metabolites of LSD, including O-H-LSD. Besides LSD, other prodrugs of LSD have been described or are being developed. The method can also be used to determine amounts of LSD and O-H-LSD after administration of any other prodrug of LSD or any other LSD analog that results in the same metabolites. Furthermore, the method can be adjusted to include the analysis of other ergotamine compounds. This includes the analytical method as well as the concept of TDM for LSD-analog-assisted psychotherapy.

"LC-MS/MS" as used herein, refers to a liquid chromatography-tandem mass spectrometry analytical chemistry technique.

The present invention provides for a method of measuring and identifying LSD and its metabolite O-H-LSD by obtaining a sample from an individual and measuring and identifying the analytes in the sample by performing a LC-MS/MS analysis. In contrast to existing LC-MS/MS methods the present invention can processes the samples in a less laborious manner and requires therefore less time for the analysis. Therefore, a well-plate containing 96 samples can be processed within 40 minutes. That includes two steps, a sample extraction (addition of extraction solvent to each sample) and 30 minutes centrifugation of the plate. Moreover, the analysis time of a sample, the chromatographic run, is shorter than almost all existing methods, qualifying the present method for high throughput analyses. Run time for analysis can be 4 minutes per sample.

The present invention requires considerably less sample material and is still more or at least equally sensitive than other known methods. The amount of sample needed to be obtained from the subject is 300 µL, which is a sufficient amount of material if re-analyses have to be performed. 50 µL of sample can be used in the actual LC-MS/MS method. In terms of absolute sensitivity, the present invention can quantify 0.5 pg LSD, whereas the quantification limit of existing methods is larger than 2.5 pg. This low quantification limit allows to quantify plasma levels of LSD after administration of microdoses of LSD, which could not be validly measured with existing methods. This high sensitivity also allows quantifying plasma levels of LSD longer after administration of any dose of LSD and expanding the window of a positive documentation of past LSD use using human plasma. Quantification with the method can be up to six hours after administration. Importantly, methods using the same type of tandem mass spectrometer, an API 5500, did not reach our quantification limits, pointing out that our extraction and chromatographic approach is advantageous compared to others (Grumann et al., 2019) (Steuer et al., 2017). Finally, the present invention will be important to set-up reference PK data for later TDM. This analytical method and the associated TDM application can be used to identify individuals who have taken LSD, and whether LSD levels are in the therapeutic range. Dosing of the LSD can be adjusted in the individual as needed based on the amount of LSD quantified in the method. Additionally, simultaneous determination of O-H-LSD can be used to interpret drug-drug interactions or the influence of diseases such as liver or kidney insufficiency on the PK properties of LSD.

A thorough development and full validation according to regulatory bioanalytical guidelines (FDA/EMA) of an LC-MS/MS method is provided for the analysis of LSD and O-H-LSD in human (EMA, 2011; FDA, 2018). Herein, a state-of-the-art LC-MS/MS method is described to investigate the PK of LSD and O-H-LSD. The method provides advantages over other prior art methods as it is at least 5-times more sensitive, uses small amounts of sample, involves an uncomplicated extraction protocol, and includes rapid sample analysis. In order to accomplish the aforementioned methodological advantages, plasma proteins were precipitated with acetonitrile. Afterwards, the samples were centrifuged to solidify the precipitate on the bottom of the analysis tube, permitting injection of the protein free supernatant into the LC-MS/MS system. The injected samples were diluted online via a T-union installed in front of the analytical column, enhancing the interaction with the column. A pH resistant analytical column was selected so as to use a high pH of 9.0 for mobile phase A. This further improved the attraction and retention of LSD to the column and hence also the sensitivity of the method. Overall, a semi-automated workflow to extract and analyze samples in 96-well plate format is operable with the present invention, facilitating high-throughput analysis. Relevantly, the method was put into practice and the clinical application of the method was demonstrated by assessing the PK of LSD microdoses in healthy participants in a clinical study. It was thereby demonstrated that lowest dosages of 5 µg LSD can effortlessly be monitored over a long period in human plasma.

LSD is prototype hallucinogenic drug, which is investigated as a medication to treat a range of psychiatric disorders (Gasser et al., 2014; Liechti, 2017). The pharmacokinetic properties of LSD in particular at low doses are not sufficiently characterized with only two preliminary studies (Family et al., 2020; Holze et al., 2021a). There is a need for validly and rapidly measuring LSD plasma levels to analyze human plasma samples from pharmacokinetics studies and other clinical trials. O-H-LSD is a main inactive metabolite of LSD, which is largely renally eliminated.

Once LSD is marketed and regularly used in patients there is a need to determine plasma concentrations for TDM. For example, plasma levels of the drug can be determined in patients not responding to usual doses of LSD to adjust dosing. However, a method is needed to reliably and rapidly measure LSD concentration in plasma allowing to provide physicians with such information. Therefore, the method must be uncomplicated to be practical for routine analyses. Additionally, LSD to O-H-LSD metabolic ratios may be used to identify slow or rapid metabolizers. Metabolic ratios will also be helpful to adjust doses in case patients suffer from kidney or liver insufficiency. Finally, LSD and O-H-LSD levels can be used to diagnose intoxications. Therefore, the present invention was developed and validated and includes a rapid LC-MS/MS method to quantify LSD and O-H-LSD in human plasma. Plasma samples were processed by protein precipitation using acetonitrile. The injected sample was mixed with aqueous solution of ammonium bicarbonate (pH 9) in front of the pH stable $C_{18}$ analytical column to increase retention of the analytes. LSD and O-H-LSD were detected by multiple reaction monitoring in positive and negative electrospray ionization mode, respectively.

The present invention provides for a method of treating and monitoring individuals taking LSD, by administering a microdose of LSD, a prodrug of LSD, or an analog of LSD to the individual, monitoring the individual by obtaining a sample from an individual and measuring and identifying the analytes in the sample by performing a LC-MS/MS analysis, and adjusting the microdose based on the amount of LSD quantified in the LC-MS/MS analysis. This method can be used to slightly adjust the dosing and effects of LSD in an individual. Since a microdose is so small, there can be a dramatic variation in its efficacy or toxicity. Therefore, it is critical to measure the amount of LSD in vivo and monitor the individual to adjust dosing.

The present invention also provides generally for a method of adjusting dosing of LSD, by administering a microdose of LSD, a prodrug of LSD, or an analog of LSD to the individual, and adjusting the microdose based on blood concentration analytics. The blood concentration analytics are obtained by performing the LC-MS/MS analysis as above.

As described in EXAMPLE 1 below, an inter-assay accuracy of 94.1-104% and precision of ≥9.1% was recorded over three validation runs. The recovery was complete (≥98.3%) and importantly, consistent over different concentration levels and plasma batches (CV %: ≥3.84%). The plasma matrix caused almost no ion suppression (−10.0%) and endogenous interferences could be separated from the analytes. LSD and O-H-LSD plasma samples can be thawed and re-frozen for three cycles, kept at room temperature for 8 hours without showing degradation (≤8.83%). The linear range (R ≥0.997) of the method covered plasma concentrations observed in humans following microdoses of as low as 5 µg up to high doses of 200 µg LSD and was therefore able to assess the pharmacokinetics of LSD and O-H-LSD. The LC-MS/MS method was convenient and reliable for measuring LSD and O-H-LSD in plasma and is useful to facilitate the clinical development of LSD and TDM when LSD is used in patients.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

EXAMPLE 1

Objective

The objective of this study was to validate an analytical method for the simultaneous quantification of lysergic acid diethylamide (LSD) and 2,3-dihydro-3-hydroxy-2-oxo lysergide (O-H-LSD) in human plasma on the API 5500 QTRAP LC-MS/MS system. The method is being used for the analysis of plasma samples from clinical studies using LSD. The analyses were conducted at the University Hospital Basel.

Summary of the Bioanalytical Method

A bioanalytical method was developed and validated for the simultaneous quantification of LSD and O-H-LSD in human plasma samples by LC-MS/MS on the API 5500 QTRAP tandem mass spectrometer. Calibration (Cal) and quality control (QC) samples were prepared in human plasma. Day-to-day performance was controlled by the analysis of QC samples. The work-up of samples was carried out with 50 µl human plasma, whereas 50 µl aliquots were mixed with 150 µl internal standard (ISTD) working solution. Samples were vortex-mixed for about 1 minute and centrifuged in order to obtain a clear supernatant without plasma proteins. An aliquot of 10 µl supernatant was injected into the LC-MS/MS system. All Cal and QC samples were subjected to the same assay procedure. The lower limit of quantification (LLOQ) was set to 10 pg/ml, while the upper limit of quantification (ULOQ) was set to 10,000 pg/ml. The analytical method was validated according to criteria specified by the FDA Bioanalytical Method Validation Guidance for Industry, May 2018 (FDA, 2018).

Reference Items

The following reference substances were used for the preparation of the ISTN solution and Cal and QC samples.

TABLE 1

| Reference substances | |
|---|---|
| LSD | |
| Identity | Lysergic acid diethylamide |
| Solvent | Acetonitrile |
| Origin | Lipomed |
| Storage | −20° C. |
| Formula | C20H25N3O |
| Molecular weight | 323.44 |
| Chemical Purity | >98.5% |
| Batch number | CAL:397.1B17.1L4A |
| | QC: 397.1B17.1V4 |
| Expiry date | CAL: November 2020 |
| | QC: November 2021 |
| LSD-d3 | |
| Identity | Lysergic acid diethylamide-d3 |
| Solvent | Acetonitrile |
| Origin | Lipomed |
| Storage | −20° C. |
| Formula | C20H22D3N3O |
| Molecular weight | 326.41 |
| Chemical Purity | >95.0% |
| Isotopic purity | D0/D3: 0.1 |
| Batch number | 582.1B3.1L2A |
| Expiry date | January 2022 |
| O—H-LSD | |
| Identity | 2,3-dihydro-3-hydroxy-2-oxo lysergide |
| Solvent | DMSO |
| Origin | Toronto Research Chemicals |
| Storage | −20° C. |
| Formula | $C_{20}H_{25}N_3O_3$ |
| Molecular weight | 355.43 |
| Chemical purity | 96.0% |
| Batch number | 5-LIJ-8-3 |
| Retest date | January 2021 |

TABLE 1-continued

| Reference substances | |
|---|---|
| O—H-LSD-d10 | |
| Identity | 2,3-dihydro-3-hydroxy-2-oxo lysergide-d10 |
| Solvent | DMSO |
| Origin | Toronto Research Chemicals |
| Storage | −20° C. |
| Formula | $C_{20}H_{15}D_{10}N_3O_3$ |
| Molecular weight | 365.49 |
| Chemical purity | 94.16% |
| Isotopic purity | 98.7% |
| Batch number | 5-LIJ-10-4 |
| Expiry date | February 2022 |

Blank Human Plasma

Blank human plasma (anticoagulants: lithium heparin), was obtained by the local blood donation center (Blutspendezentrum SRK beider Basel, Hebelstrasse 10, 4056 Basel, Switzerland). The plasma was stored at about −20° C.

Apparatus, Reagents, and Materials

LC-MS/MS System

| | |
|---|---|
| Mass spectrometer | API 5500 mass spectrometer (AB Sciex, Concord, Canada) |
| Controller | CBM-20A system controller (Shimadzu, Kyoto, Japan) |
| Autosampler | SIL-30ACMP autosampler (Shimadzu, Kyoto, Japan) |
| Degasser 1 | DGU-20A5R degasser (Shimadzu, Kyoto, Japan) |
| Degasser 2 | DGU-20A3 degasser (Shimadzu, Kyoto, Japan) |
| Column oven | CTO-20AC oven (Shimadzu, Kyoto, Japan) |
| LC Pump A | LC-30AD pump (Shimadzu, Kyoto, Japan) |
| LC Pump B | LC-30AD pump (Shimadzu, Kyoto, Japan) |
| LC Pump C | LC-30AD pump (Shimadzu, Kyoto, Japan) |
| LC Pump D | LC-30AD pump (Shimadzu, Kyoto, Japan) |

Equipment

| | |
|---|---|
| Balance | Analytical balance XP26 (Mettler Toledo, Ohio, USA) |
| Centrifuge | Eppendorf 5810R centrifuge (Eppendorf, Hamburg, Germany) |
| Vortex mixer | Multi-Tube vortexer VX-2500 (VWR, Pennsylvania, USA) |
| Autosampler tubes | Matrix tubes (0.75 ml, Thermo Fisher Scientific, Massachusetts, USA) |
| Cal/QC tubes | Nunc CryoTubes (3.6 & 4.5 ml, Thermo Fisher Scientific, Massachusetts, USA) |
| Cal/QC tubes | Micro tubes (1.5 ml, Sarstedt, Nümbrecht, Germany) |

HPLC COLUMN

| | |
|---|---|
| Analytical column | Kinetex EVO C18, 1.7 µm, 50 × 2.1 mm (Phenomenex, Torrance, USA) |

Chemicals

| | |
|---|---|
| Formic acid | 98-100% for analysis (Merck, Darmstadt, Germany) |
| Methanol | LiChrosolv for chromat. (Merck, Darmstadt, Germany) |
| Acetonitrile | LiChrosolv for chromat. (Merck, Darmstadt, Germany) |
| Isopropanol | LiChrosolv for chromat. (Merck, Darmstadt, Germany) |

-continued

| | |
|---|---|
| Water | LiChrosolv for chromat. (Merck, Darmstadt, Germany) |
| Ammonium bicarbonate | LiChropur for LC-MS (Sigma-Aldrich, St. Louis, USA) |
| Ammonium hydroxide | ≥25% solution for LC-MS (Sigma-Aldrich, St. Louis, USA) |

Description of the LC-MS/MS System

Acquisition Method

| | |
|---|---|
| Acquisition name | 2018 Aug. 21 LSD_OH-LSD_NOR-LSD.dam |

Mobile Phases

| Mobile Phases | |
|---|---|
| Pump A and C | 20 mM ammonium bicarbonate in $H_2O$ (pH was adjusted to 9.0 using ammonium hydroxide solution (≥25% v/v)) |
| Pump B and D | Acetonitrile + 0.1% formic acid |

Autosampler Wash Solution

| | |
|---|---|
| Wash solution mixture: | Methanol/$H_2O$/acetonitrile/isopropanol 1/1/1/1 (v/v/v/v) |

LC-MS/MS Settings

Initial HPLC Settings

| | |
|---|---|
| Pumping mode | Binary Flow |
| Flow LC pump A and B | 0.1 ml/min |

-continued

| | |
|---|---|
| Flow LC pump C | 0.5 ml/min |
| Oven temp | 30° C. |
| Autosampler temperature | 10° C. |
| Rinsing volume | 0.5 ml before aspiration |
| Injection loop | 50 μl |
| Injected volume | 10 μl |
| MS valve | Position A (HPLC connected with the solvent waste) |

TABLE 2

HPLC pump gradient program and time events for LSD and O—H-LSD analyses

| Time | Module | Event | Parameters |
|---|---|---|---|
| 0.00 | MS Valve | Switch | A |
| 0.50 | Pumps | Pump B | 10 |
| 0.50 | Pumps | Pump C | 0 |
| 0.50 | Pumps | Total Flow | 0.6 |
| 1.00 | MS Valve | Switch | B |
| 2.75 | Pumps | Pump B | 95 |
| 3.00 | MS Valve | Switch | A |
| 3.50 | Pumps | Pump B | 95 |
| 3.51 | Pumps | Pump B | 10 |
| 4.00 | Controller | Stop | |

Between minute 1.0 to 3.0 of each run the HPLC flow was directed into the mass spectrometer (right valve position B) otherwise into the solvent waste bottle.

Retention Times of the Analytes

| | |
|---|---|
| LSD | 1.8 min |
| LSD-d3 | 1.8 min |
| O—H-LSD | 1.5 min |
| O—H-LSD-d10 | 1.5 min |

Mass Spectrometer Settings

| | |
|---|---|
| Source interface | Turbo Ion Spray (electrospray ionization) |
| Polarity | Positive |
| Run time (per sample) | 4 min |
| Scan type | MRM mode |
| Acquisition mode | Profile |

The m/z values of the different ions used to monitor the concentrations of the analytes and ISTD in human plasma are listed below in TABLE 3. A chromatogram of LSD and O-H-LSD is depict in FIG. 2.

TABLE 3

Analyte specific settings used for the analysis of LSD and O—H-LSD.

| Analyte | Q1 mass, Da | Q3 mass, Da | Time, msec | DP, V | EP, V | CE, V | CXP, V |
|---|---|---|---|---|---|---|---|
| LSD I | 324.1 | 223.2 | 15 | 131 | 10 | 33 | 20 |
| LSD II | 324.1 | 207.1 | 15 | 131 | 10 | 57 | 16 |
| LSD-$d_3$ I | 327.1 | 226.2 | 15 | 126 | 10 | 33 | 16 |
| LSD-$d_3$ II | 327.1 | 210.1 | 15 | 126 | 10 | 63 | 14 |
| O—H-LSD I | 356.1 | 222.0 | 15 | 161 | 10 | 41 | 16 |
| O—H-LSD II | 356.1 | 237.0 | 15 | 161 | 10 | 33 | 16 |
| O—H-LSD-$d_{10}$ I | 366.2 | 222.0 | 15 | 176 | 10 | 45 | 18 |
| O—H-LSD-d10 | 366.2 | 237.2 | 15 | 176 | 10 | 35 | 16 |

FIG. 2 is a chromatogram of LSD (5000 pg/ml) and O-H-LSD (5000 pg/ml) in human plasma. LSD-$d_3$ and O-H-LSD-$d_{10}$ were used as internal standards. LSD and O-H-LSD eluted after 1.78 and 1.51 minutes, respectively. The chromatogram was recorded on Jul. 21, 2020.

Data Acquisition and Calculation

Sample lists, acquisition method, data collection, and quantification were generated with Analyst software (version 1.7.1) from AB Sciex. The concentrations of LSD and O-H-LSD in Cal and QC samples were calculated by the internal standardization method. Data for the mean, standard deviation, accuracy and precision for Cal and QC samples were calculated with Excel Office 365 from Microsoft (Washington, USA).

Data Reporting

Assay results for the analytes were rounded to three significant digits. Concentrations below 10 pg/ml were reported as "blq".

Preparation of Stock and Working Solutions

The concentrations of the solutions are based on the free and unionized form of the drug. All solutions were prepared in 1.5 ml micro tubes (Sarstedt, Nümbrecht, Germany).

LSD Stock Solutions

Stock Solutions for Cal Samples: 0.1 mg/ml of LSD in Acetonitrile

A solution of 0.1 mg/ml LSD in acetonitrile was purchased from Lipomed (Arlesheim, Switzerland).

Stock Solutions for QC Samples: 1 mg/ml of LSD in Acetonitrile

An exact weight of 1.0 mg LSD was purchased from Lipomed (Arlesheim, Switzerland) and dissolved in 985 µl acetonitrile (LSD purity: 98.5%).

ISTD Stock Solutions: 0.1 mg/ml LSD-$d_3$ in Acetonitrile

A solution of 0.1 mg/ml LSD-$d_3$ in acetonitrile was purchased from Lipomed (Arlesheim, Switzerland).

Working Solutions

Stock Solution Mix for Cal Samples (Mix-C): 2500 ng/ml of LSD and O-H-LSD

LSD (0.1 mg/ml) and O-H-LSD (1 mg/ml) stock solutions were individually diluted to a final concentration of 10 µg/ml in DMSO. Therefore, 50 µl of LSD (0.1 mg/ml) was mixed with 450 µL DMSO and 10 µl of O-H-LSD (1 mg/ml) was added to 990 µl DMSO. Afterwards, 250 µL of each working solution (10 µg/ml) was mixed with 500 µL of DMSO. The resulting solution has a concentration of 2500 ng/ml LSD and O-H-LSD.

Stock Solution Mix for QC Samples (Mix-Q): 2500 ng/ml of LSD and O-H-LSD.

LSD and O-H-LSD stock solutions (1 mg/ml) were individually diluted to a final concentration of 10 µg/ml in DMSO. Therefore, 10 µl of each stock solution was added to 990 µL of DMSO. Afterwards, 250 µL of each working solution (10 µg/ml) was mixed with 500 µL of DMSO. The resulting solution has a concentration of 2500 ng/ml LSD and O-H-LSD.

The above preparations were shaken until complete dissolution and afterwards stored in the freezer at −20° C.

Preparation of Calibration Samples

Ten Cal samples with concentrations ranging from 10 to 10000 pg/ml were prepared using Mix-C working solution. The dilution procedure is reported in TABLES 4A and 4B.

TABLES 4A and 4B

| | Preparation of Cal samples | | | | | | | | |
|---|---|---|---|---|---|---|---|---|---|
| | A. CAL working solutions prepared in DMSO | | | | | B. CAL samples prepared in human plasma | | | |
| ID | Conc. in DMSO (ng/ml) | $V_{Analyte}$ [µl] | $V_{DMSO}$ [µl] | $V_{tot}$ [µl] | → | Conc. in plasma (pg/ml) | $V_{CAL}$ [µl] | $V_{Plasma}$ [µl] | $V_{tot}$ [µl] |
| Mix-C | 2500 | — | — | — | | — | — | — | — |
| CAL 1 | 1000 | 400 | 600 | 1000 | | 10000 | 20 | 1980 | 2000 |
| CAL 2 | 500 | 500 | 500 | 1000 | | 5000 | 20 | 1980 | 2000 |
| CAL 3 | 250 | 500 | 500 | 1000 | | 2500 | 20 | 1980 | 2000 |
| CAL 4 | 100 | 400 | 600 | 1000 | | 1000 | 20 | 1980 | 2000 |
| CAL 5 | 50 | 500 | 500 | 1000 | | 500 | 20 | 1980 | 2000 |
| CAL 6 | 25 | 500 | 500 | 1000 | | 250 | 20 | 1980 | 2000 |
| CAL 7 | 10 | 400 | 600 | 1000 | | 100 | 20 | 1980 | 2000 |
| CAL 8 | 5 | 500 | 500 | 1000 | | 50 | 20 | 1980 | 2000 |
| CAL 9 | 2.5 | 500 | 500 | 1000 | | 2.5 | 20 | 1980 | 2000 |
| CAL 10 | 1 | 400 | 600 | 1000 | | 10 | 20 | 1980 | 2000 |

O-H-LSD Stock Solutions

Stock solutions for Cal samples: 1 mg/ml of O-H-LSD in DMSO

An exact weight of 1.094 mg O-H-LSD was purchased from Toronto Research Chemicals (Ontario, Canada) and dissolved in 1050 µl DMSO (O-H-LSD purity: 96%).

Stock Solutions for QC Samples: 1 mg/ml of O-H-LSD in DMSO

An exact weight of 1.233 mg O-H-LSD was purchased from Toronto Research Chemicals (Ontario, Canada) and dissolved in 1184 µl DMSO (O-H-LSD purity: 96%).

ISTD Stock Solutions: 1 mg/ml O-H-LSD-$d_{10}$ in -MSO

A weight of 1 mg of O-H-LSD-$d_{10}$ was dissolved in 1000 µl with DMSO.

The above preparations were shaken until complete dissolution and afterwards stored in the freezer at −20° C.

Working solutions were stored in 1.5 ml micro tubes (Sarstedt, Germany) at about −20° C. (TABLE 4A). The volumes reported in TABLE 4B were used to prepare 2 ml Cal samples in human plasma. Aliquots of 50 µl were stored in 0.75 ml micro tubes at about −20° C.

Preparation of Quality Control Samples

QC samples at five different concentrations of LSD and O-H-LSD were prepared using Mix-Q working solution. Working solutions were prepared as described in TABLE 5A, while QCs in plasma were prepared according to TABLE 5B.

TABLES 5A and 5B

Preparation of QC samples

| | A. QC working solutions prepared in DMSO | | | | → | B. QC samples prepared in human plasma | | | |
|---|---|---|---|---|---|---|---|---|---|
| ID | Conc. in DMSO (ng/ml) | $V_{Analytes}$ [µl] | $V_{DMSO}$ [µl] | $V_{tot}$ [µl] | | Conc. in plasma (pg/ml) | $V_{QC}$ [µl] | $V_{Plasma}$ [µl] | $V_{tot}$ [µl] |
| MIX-Q | 2500 | — | — | — | | | | | |
| ULOQ | 1000 | 400 | 600 | 1000 | | 10000 | 40 | 3960 | 4000 |
| $QC_{High}$ | 100 | 100 | 900 | 1000 | | 1000 | 40 | 3960 | 4000 |
| $QC_{MID}$ | 10 | 100 | 900 | 1000 | | 100 | 40 | 3960 | 4000 |
| $QC_{LOW}$ | 2.5 | 250 | 750 | 1000 | | 25 | 40 | 3960 | 4000 |
| LLOQ | 1.0 | 400 | 600 | 1000 | | 10 | 40 | 3960 | 4000 |

Working solutions were stored in 1.5 ml micro tubes (Sarstedt, Germany) at about −20° C. (TABLE 5A). The volumes reported in TABLE 5B were used to prepare 4 ml QC samples in human plasma. Aliquots of 50 µl were stored in 0.75 ml Thermo micro tubes at about −20° C.

Preparation of Internal Standard Solutions

ISTD Working Solution: 100 pg/ml LSD-$d_3$ and 250 pg/ml O-H-LSD-$d_{10}$ in Acetonitrile 50 µl LSD-$d_3$ stock solution (0.1 mg/ml) was prepared in 450 µl acetonitrile to receive a working solution of 10 µg/ml. 10 µl of O-H-LSD-$d_{10}$ stock solution (1 mg/ml) was prepared in 990 µl acetonitrile to receive a solution of 10 µg/ml.

5 µL of LSD-$d_3$ working solution (10 µg/ml) and 12.5 µL of O-H-LSD-$d_{10}$ working solution (10 µg/ml) were added to 500 ml acetonitrile to receive a solution of 100 pg/ml and 250 pg/ml, respectively. The solution was stored at about −20° C.

Sample Extraction

Plasma samples used for validation runs were thawed and worked up as stated below at 1-4.
1. Thaw the individual Cal and QC samples (50 µl aliquots).
2. Add 150 µl ISTD (Blank: acetonitrile).
3. Vortex for at least 30 seconds.
4. Centrifuge at 10° C. and 3220 g for 30 minutes.

Worked-up samples were stored at about 10° C. if not used immediately.

Principles and Calculations

Composition of an Analytical and Validation Run

An analytical run included two sets of ten Cal samples, two double Blank samples (without ISTD), two Blank samples (with ISTD) and at least three QC samples at three different concentrations (low, medium, and high concentration). For a validation run seven QC samples at five concentration levels (LLOQ, $QC_{LOW}$, $QC_{MID}$, $QC_{HIGH}$, ULOQ) were investigated. The QC samples were placed between the two sets of Cal samples. Blank samples were run before and after the calibrations. The Cal and QC samples were worked up and analyzed in the same way.

Acceptance Criteria for a Validation Run

The following conditions must be met:

The percent deviation of the lowest calibration point of the nominal value must be within ±20%.

The percent deviation of the other Cal samples of the nominal value must be within ±15%.

At least 75% of all Cal samples (including one highest and one lowest) must fulfill the above criteria.

The correlation coefficient (R) for the Cal curve must be greater than 0.99.

≥67% (e.g., five out of 7) of the QC samples of one concentration level must be within ±15% of their theoretical value. Concentrations had to be within ±20% for the LLOQ.

The analyte signal intensity in double Blank samples must be less than 20% of the limit of quantification signal.

Acceptance Criteria for an Analytical Run

≥67% (e.g. five out of seven) of all QC samples must be within ±15% of the theoretical values. 33% of the QC samples (not all replicates at the same concentration) can be outside ±15% of the theoretical values, otherwise the run is re-injected or completely reanalyzed.

Calculation of Calibration Samples

MultiQuant software (version 3.0.3) was used to perform a linear regression by plotting measured peak area ratios of each analyte and the respective deuterated ISTD against the nominal concentration. LSD-$d_3$ was used to normalize the LSD response, whereas O-H-LSD-$d_{10}$ was used for O-H-LSD normalization. A weighting factor of $1/x^2$ was selected for the linear regressions. All Cal samples that fulfill the specifications were used to generate the standard calibration curve. This means for a valid run a standard calibration curve consisted of at least fifteen to a maximum of twenty Cal samples. Cal samples, which were out of specifications, were not used for any further calculations.

Calculation of Quality Control Samples

The calibration curve equation was used to back calculate the concentrations of LSD and O-H-LSD in QC samples by using the corresponding peak-area ratios. The obtained value of each QC sample was checked against the acceptance criteria.

Calculation of Study Performance

Precision

Precision is determined as intra- and inter-assay reproducibility. Mean, standard deviation and percentage relative standard deviation (% CV), were calculated for each QC concentration (intra-assay) and over three validation runs (inter-assay).

Accuracy

Accuracy was calculated from the overall mean of each QC level divided by its nominal value within each assay (intra-assay) and over three validation runs (inter-assay).

Selectivity I

In drug free human plasma of at least six different specimens, there should not be interferences which are greater than 20% of the analyte peak area at the LLOQ level.

Selectivity II

The mean accuracy of at least six samples of different specimens at the LLOQ level should be within 80-120%. The accuracy of ≥67% (e.g. five out of seven) of those samples must be within 80-120%.

Carry-Over

The carry-over between samples was determined by injecting an ULOQ sample followed by two double Blank samples. The signal intensity of the analyte peak of the double Blank samples was compared with the signal intensity measured at ULOQ level. The total carry-over of the employed analysis system accounts usually for about 0.1%. In addition, the analyte peak area of the double Blank samples was compared with the peak area determined at the LLOQ level. The carry-over should be less than 20% of the LLOQ peak area, otherwise additional solvent samples have to be included for the analysis of study samples.

Recovery and Matrix Effect

Recovery of the analytes and internal standards should be consistent, precise and reproducible according to the used guidelines (FDA, 2018).

Matrix effect should be consistent over at least six lots of matrix. The % CV of the matrix effect calculated from at least 6 lots of matrix should not be greater than 15%. This determination should be done at least at low and high concentration levels (EMA, 2011).

Stability Tests

Each analyte had to be stable in human plasma for at least three freeze-thaw cycles (for repeated sample preparations) and at ambient temperature for at least eight hours (maximal duration of sample preparation). Measured samples should be stable for a second injection when the first analytical run was not valid. The analytes had to be stable in the matrix at the intended storage temperatures and study duration.

An analyte was considered stable at one of the above tests when no increase or decrease of the analyte concentration of more than 15% for the mean of at least three analyzed QC samples at low, medium and at high concentration was observed.

Description of Experiments

Validation Runs

Three valid validation runs were worked up on three different days. Each run consisted of two calibration curves (one at the beginning and one at the end of the validation run), two double Blank samples, two Blank samples, and 35 QC samples at five concentration levels. QC levels included the LLOQ (10 pg/ml), $QC_{LOW}$ (25 pg/ml), $QC_{MID}$ (100 pg/ml), $QC_{HIGH}$ (1000 pg/ml), and the ULOQ (10000 pg/ml) concentration level. Two double Blank samples were measured directly after the analysis of an ULOQ sample in order to determine the carry-over of the method.

Selectivity I

Double Blank and Blank human plasma from seven different subjects were worked-up and analyzed during the validation run.

Selectivity II

Seven Blank plasma samples from different subjects were spiked with the analytes at the LLOQ, processed, and analyzed. The intra-assay accuracy and precision of the samples were assessed based on two calibration curves (one measured at the beginning and one at the end of the validation run).

Recovery and Matrix Effect

For the determination of the recovery from human plasma the peak areas of worked-up QC samples (samples spiked before extraction) were compared with the peak areas of worked-up Blank plasma samples (supernatants), which were spiked with the nominal analyte concentrations of QCLOW, QCMID, QCHIGH, and QCULOQ (samples spiked after extraction). The peak area found in the spiked supernatants corresponded to 100% recovery and was compared to the corresponding peak area of spiked and processed plasma samples.

The matrix effect was determined for at least six different lots of matrix, by calculating the ratio of the peak area in the presence of matrix (measured by analyzing Blank plasma spiked with analyte after extraction), to the peak area in absence of matrix using water instead of plasma. This determination was done at QCLOW, QCMID, QCHIGH, and ULOQ.

Stability Tests

Reinjection Reproducibility

Worked-up and measured Cal and QC samples (prepared in human plasma) of a valid run were repeatedly analyzed. Reinjection was performed after overnight storage at 10° C. (autosampler) and after 1-week storage at −20° C. The run was checked according to the acceptance criteria for validation runs. The calculated mean values for QC samples were compared between the original and reinjected run.

Bench-Top Stability Tests

Seven of each LLOQ, QCLOW, QCMID, QCHIGH, and ULOQ samples in human plasma were thawed at ambient temperature and kept at this temperature for 8 hours. Afterwards, the samples were worked up and analyzed. The values of the concentrations in the "short-term" samples were compared with freshly processed QC samples. Concentrations were calculated based on two freshly prepared CAL sets measured at the beginning and the end of the validation run.

Freeze/Thaw Stability Tests

Seven of each LLOQ, QCLOW, QCMID, QCHIGH, and ULOQ sample in human plasma were stored at about −20° C. for at least 24 hours and thawed unassisted at ambient temperature. When completely thawed, the samples were refrozen for at least 12 hours under the same conditions. The freeze-thaw cycle was repeated two more times. After the third cycle the samples were worked up and analyzed. The concentrations in the frozen and thawed samples were compared with freshly processed QC samples. Concentrations were calculated based on two freshly prepared CALs measured at the beginning and the other at the end of the validation run.

Method Application

To examine the application of the developed method, LSD and O-H-LSD concentrations were quantified in plasma samples of three healthy volunteers receiving a single oral dose of 5 μg. This corresponds to a very low LSD dose, used in LSD microdosing clinical trials (Holze et al., 2021a). The study was conducted in accordance with the Declaration of Helsinki and approved by the Medical Ethics Committee of the Academic Hospital of Maastricht and Maastricht University. The use of LSD in humans was authorized by the Dutch Drug Enforcement Administration. All volunteers provided written informed consent prior to study participation. To establish concentration time profiles, blood samples were collected in lithium heparin coated tubes at the following time points: 0, 0.5, 1, 1.5, 2, 3, 4, 6 after treatment. Blood samples were centrifuged, and plasma was frozen at −20° C. until analysis.

Results of the Method Validation and Application

A sensitive LC-MS/MS method was developed and fully validated with a simple and fast sample analysis workflow.

Method Validation

Validation Runs: Method Linearity, Accuracy, and Precision

LSD

Figure 3A:
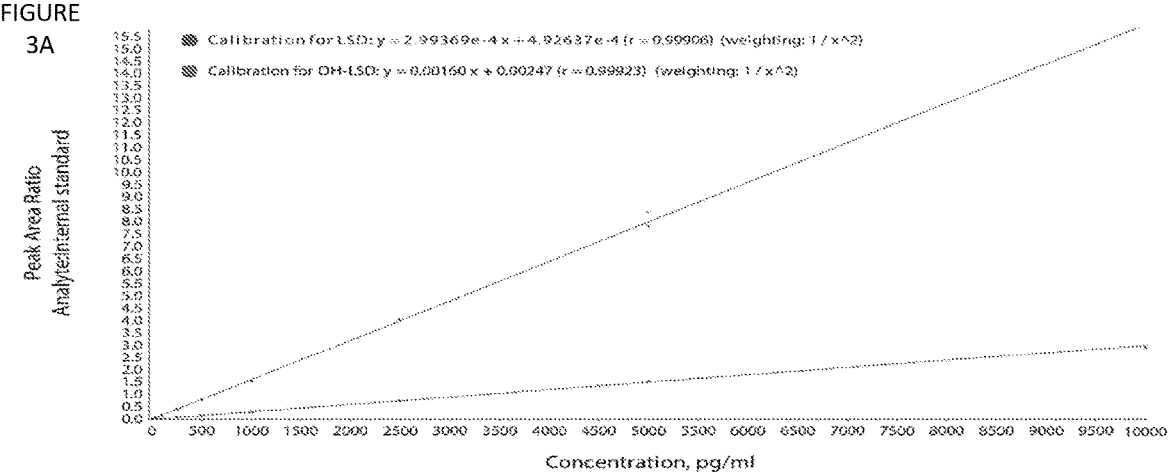
FIGS. 3A-3C are graphs showing the calibration line of LSD and O-H-LSD in human plasma (FIG. 3A on Jul. 18, 2020, FIG. 3B on Jul. 20, 2020, and FIG. 3C on Jul. 21, 2020)
Figure 3B:
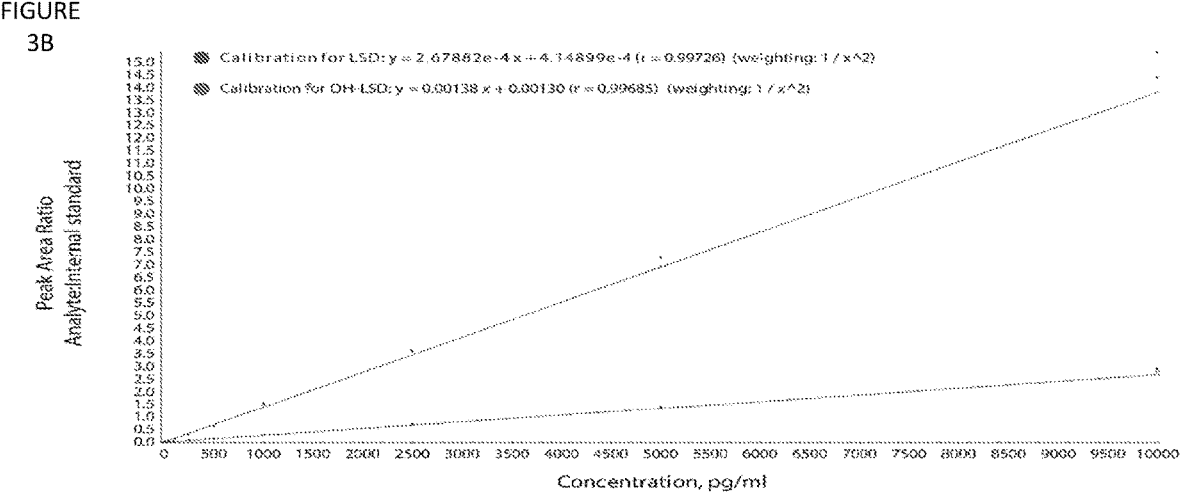
Figure 3C:
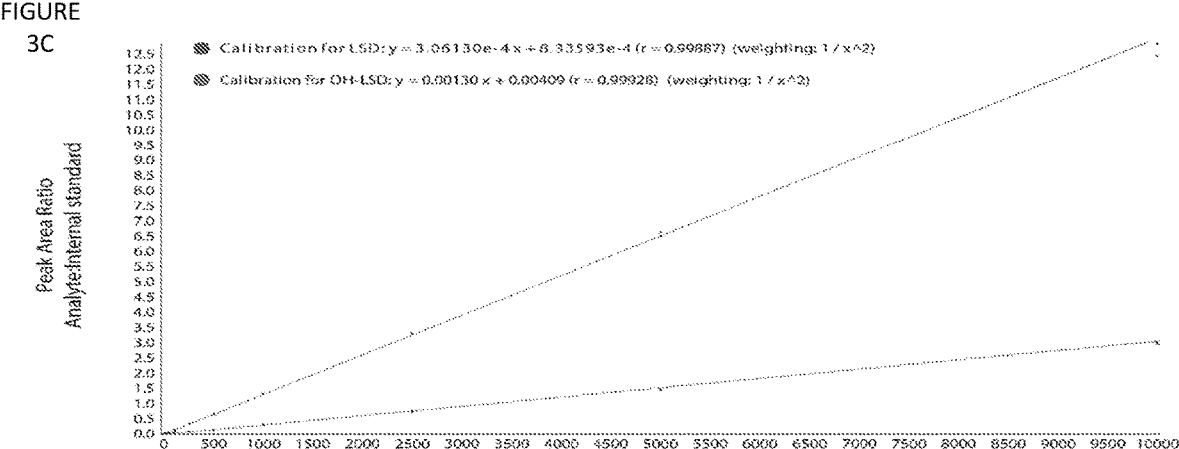
Figure 4A:
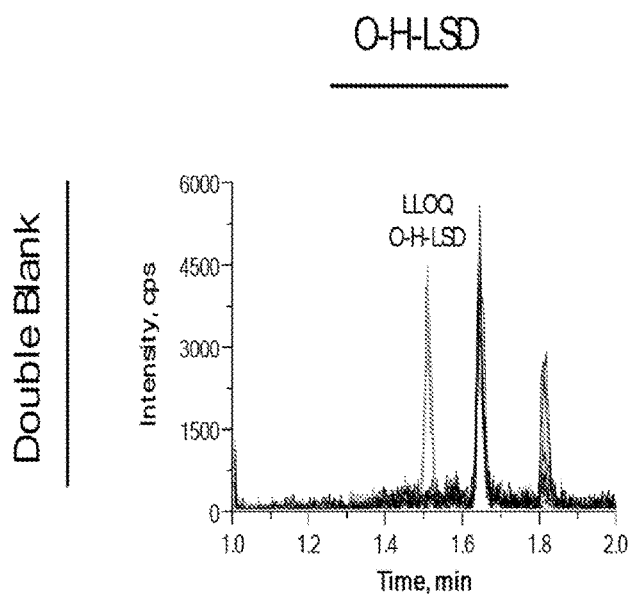
FIGS. 4A-4D are graphs demonstrating that LSD and O-H-LSD can be selectively determined in human plasma processed with (blank) and without internal standard (double blank), an overlay of seven O-H-LSD (FIG. 4A) and LSD (FIG. 4B) double Blank (thick black line) and LLOQ (dashed line) chromatograms is shown, and an overlay of seven O-H-LSD (FIG. 4C) and LSD (FIG. 4D) blank (thick black line) and LLOQ (dashed line) chromatograms is shown.
Figure 4B:
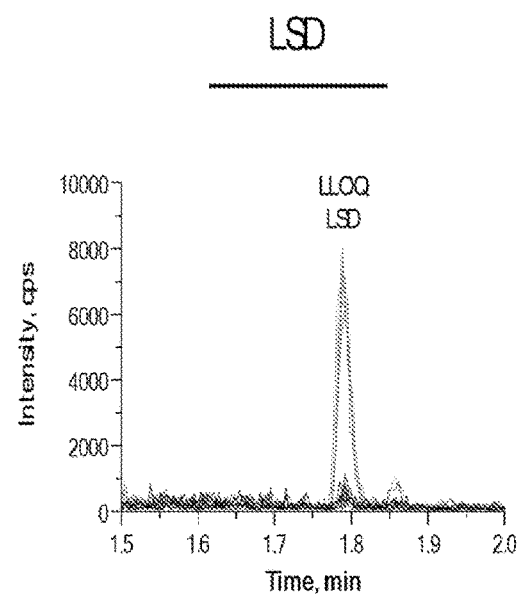
Figure 4C:
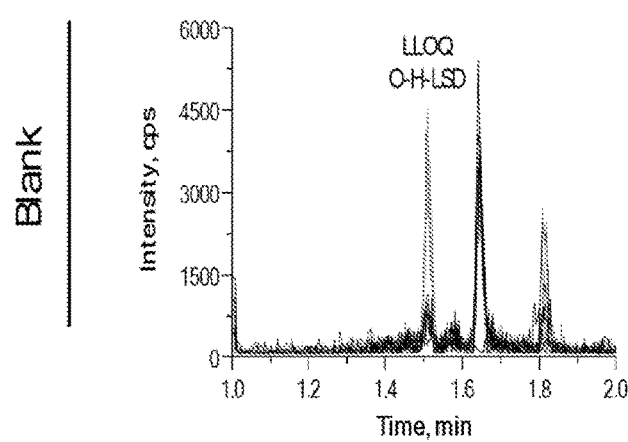
Figure 4D:
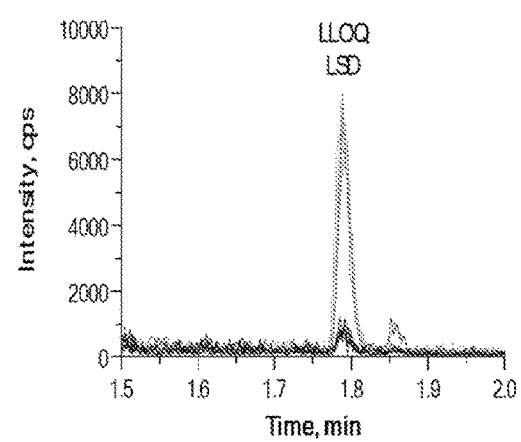

All calibration curves of the three validation runs were valid (TABLE 6). All calibration curves were linear, the correlation coefficients were ≥0.997 (FIGS. 3A-3C). During the validation runs a total of 105 QC samples were analyzed. Of these 105 QC samples 100 fulfilled the specifications for QC samples (TABLE 8).

O-H-LSD

All calibration curves of the three validation runs were valid (TABLE 7). All calibration curves were linear, the correlation coefficients were ≥0.997 for all the runs (FIGS. 3A-3C). During the validation runs a total of 105 QC samples were analyzed. Of these 105 QC samples 99 fulfilled the specifications for QC samples (TABLE 9).

TABLE 6

Accuracy and precision data of LSD calibration curves

| LSD Actual Concentration (pg/ml) | Value #1 (pg/ml) | Value #2 (pg/ml) | Mean (pg/ml) | SD (pg/ml) | CV (%) | Accuracy (%) | Num. Values |
|---|---|---|---|---|---|---|---|
| Assay 1 | | | | | | | |
| 10 | 9.56 | 9.88 | 9.72 | 0.23 | 2.33 | 97.2 | 2 of 2 |
| 25 | 25.3 | 26.6 | 25.9 | 0.92 | 3.54 | 104 | 2 of 2 |
| 50 | 54.5 | 52.1 | 53.3 | 1.66 | 3.11 | 107 | 2 of 2 |
| 100 | 103 | 98.1 | 100 | 3.35 | 3.33 | 100 | 2 of 2 |
| 250 | 248 | 253 | 251 | 3.74 | 1.49 | 100 | 2 of 2 |
| 500 | 497 | 486 | 491 | 7.77 | 1.58 | 98.3 | 2 of 2 |
| 1000 | 958 | 929 | 943 | 20.4 | 2.16 | 94.3 | 2 of 2 |
| 2500 | 2520 | 2540 | 2530 | 10.9 | 0.43 | 101 | 2 of 2 |
| 5000 | 5030 | 5110 | 5070 | 52.3 | 1.03 | 101 | 2 of 2 |
| 10000 | 9700 | 9640 | 9670 | 44.6 | 0.46 | 96.7 | 2 of 2 |
| Assay 2 | | | | | | | |
| 10 | 9.73 | 10.8 | 10.3 | 0.77 | 7.48 | 103 | 2 of 2 |
| 25 | 22.5 | 24.8 | 23.6 | 1.64 | 6.95 | 94.5 | 2 of 2 |
| 50 | 52 | 50.7 | 51.4 | 0.89 | 1.74 | 103 | 2 of 2 |
| 100 | 92.7 | 93.8 | 93.2 | 0.77 | 0.83 | 93.2 | 2 of 2 |
| 250 | 235 | 223 | 229 | 8.21 | 3.58 | 91.6 | 2 of 2 |
| 500 | 467 | 466 | 466 | 0.97 | 0.21 | 93.3 | 2 of 2 |
| 1000 | 1080 | 1070 | 1080 | 4.96 | 0.46 | 108 | 2 of 2 |
| 2500 | 2550 | 2650 | 2600 | 67.5 | 2.6 | 104 | 2 of 2 |
| 5000 | 5150 | 5190 | 5170 | 29.4 | 0.57 | 103 | 2 of 2 |
| 10000 | 10900 | 10500 | 10700 | 254 | 2.37 | 107 | 2 of 2 |
| Assay 3 | | | | | | | |
| 10 | 9.58 | 10.4 | 9.97 | 0.55 | 5.52 | 99.7 | 2 of 2 |
| 25 | 25 | 23.6 | 24.3 | 0.96 | 3.93 | 97.3 | 2 of 2 |
| 50 | 55.1 | 59.7* | 55.1 | N/A | N/A | 110 | 1 of 2 |
| 100 | 108 | 188* | 108 | N/A | N/A | 108 | 1 of 2 |
| 250 | 247 | 259 | 253 | 8.41 | 3.33 | 101 | 2 of 2 |
| 500 | 489 | 519 | 504 | 21.6 | 4.29 | 101 | 2 of 2 |
| 1000 | 1010 | 1010 | 1010 | 1.13 | 0.11 | 101 | 2 of 2 |
| 2500 | 2390 | 2460 | 2430 | 49.7 | 2.05 | 97.2 | 2 of 2 |
| 5000 | 4890 | 4800 | 4850 | 59.3 | 1.22 | 96.9 | 2 of 2 |
| 10000 | 9680 | 9850 | 9770 | 119 | 1.21 | 97.7 | 2 of 2 |

*out of the range of 85-115% (80-120% for LLOQ), not used for calculations

TABLE 7

Accuracy and precision data of O—H-LSD calibration curves

| O—H-LSD Actual Concentration (pg/ml) | Value #1 (pg/ml) | Value #2 (pg/ml) | Mean (pg/ml) | SD (pg/ml) | CV (%) | Accuracy (%) | Num. Values |
|---|---|---|---|---|---|---|---|
| Assay 1 | | | | | | | |
| 10 | 9.76 | 9.94 | 9.85 | 0.13 | 1.29 | 98.5 | 2 of 2 |
| 25 | 24.4 | 26 | 25.2 | 1.14 | 4.53 | 101 | 2 of 2 |
| 50 | 52.5 | 52.6 | 52.6 | 0.04 | 0.08 | 105 | 2 of 2 |

TABLE 7-continued

Accuracy and precision data of O—H-LSD calibration curves

| O—H-LSD Actual Concentration (pg/ml) | Value #1 (pg/ml) | Value #2 (pg/ml) | Mean (pg/ml) | SD (pg/ml) | CV (%) | Accuracy (%) | Num. Values |
|---|---|---|---|---|---|---|---|
| 100 | 104 | 101 | 103 | 2.35 | 2.29 | 103 | 2 of 2 |
| 250 | 255 | 240 | 248 | 10.5 | 4.25 | 99.1 | 2 of 2 |
| 500 | 481 | 498 | 490 | 11.7 | 2.39 | 97.9 | 2 of 2 |
| 1000 | 951 | 952 | 951 | 0.44 | 0.05 | 95.1 | 2 of 2 |
| 2500 | 2540 | 2540 | 2540 | 5.18 | 0.2 | 102 | 2 of 2 |
| 5000 | 5250 | 4910 | 5080 | 235 | 4.62 | 102 | 2 of 2 |
| 10000 | 9880 | 9630 | 9750 | 180 | 1.85 | 97.5 | 2 of 2 |
| Assay 2 | | | | | | | |
| 10 | 10.2 | 10.1 | 10.2 | 0.12 | 1.13 | 102 | 2 of 2 |
| 25 | 26.9 | 23.8 | 25.3 | 2.16 | 8.53 | 101 | 2 of 2 |
| 50 | 48.4 | 46.9 | 47.6 | 1.03 | 2.16 | 95.3 | 2 of 2 |
| 100 | 94.7 | 86.7 | 90.7 | 5.67 | 6.25 | 90.7 | 2 of 2 |
| 250 | 242 | 227 | 234 | 10.9 | 4.64 | 93.8 | 2 of 2 |
| 500 | 475 | 455 | 465 | 14.1 | 3.03 | 93 | 2 of 2 |
| 1000 | 1080 | 1100 | 1090 | 19 | 1.74 | 109 | 2 of 2 |
| 2500 | 2640 | 2590 | 2620 | 35.2 | 1.35 | 105 | 2 of 2 |
| 5000 | 5280 | 5000 | 5140 | 194 | 3.77 | 103 | 2 of 2 |
| 10000 | 11100 | 10400 | 10800 | 501 | 4.64 | 108 | 2 of 2 |
| Assay 3 | | | | | | | |
| 10 | 10.4 | 9.97 | 10.2 | 0.29 | 2.82 | 102 | 2 of 2 |
| 25 | 25.2 | 23.9 | 24.5 | 0.98 | 3.99 | 98.2 | 2 of 2 |
| 50 | 48.6 | 46 | 47.3 | 1.84 | 3.88 | 94.6 | 2 of 2 |
| 100 | 96.9 | 101 | 98.8 | 2.77 | 2.8 | 98.8 | 2 of 2 |
| 250 | 253 | 263 | 258 | 7.11 | 2.76 | 103 | 2 of 2 |
| 500 | 521 | 493 | 507 | 19.7 | 3.88 | 101 | 2 of 2 |
| 1000 | 1030 | 1030 | 1030 | 3.23 | 0.31 | 103 | 2 of 2 |
| 2500 | 2520 | 2560 | 2540 | 24.3 | 0.96 | 102 | 2 of 2 |
| 5000 | 4980 | 5080 | 5030 | 73.7 | 1.46 | 101 | 2 of 2 |
| 10000 | 9850 | 9560 | 9710 | 205 | 2.12 | 97.1 | 2 of 2 |

FIGS. 3A-3C are calibration curves of LSD and O-H-LSD in human plasma. Linearity was observed over a concentration range of 10 to 10000 pg/ml with a high correlation coefficient of ≥0.997. Analyses were performed on July 18 (A), 20 (B), and 21 (C) 2020. The developed method achieves a lower limit of quantification of 10 pg/ml and presents a linear relationship between analyte signal and concentration from 10 to 10000 pg/ml.

TABLE 8

Intra- and inter-assay precision and accuracy of LSD

| Value #1 (pg/ml) | Value #2 (pg/ml) | Value #3 (pg/ml) | Value #4 (pg/ml) | Value #5 (pg/ml) | Value #6 (pg/ml) | Value #7 (pg/ml) | Mean (pg/ml) | SD (%) | CV (%) | Accuracy (%) | Num. Values |
|---|---|---|---|---|---|---|---|---|---|---|---|
| Assay 1 | | | | | | | | | | | |
| 9.82 | 10.5 | 10.5 | 9.08 | 8.65 | 8.15 | 9.45 | 9.45 | 0.9 | 9.49 | 94.5 | 7 of 7 |
| 23.3 | 22.3 | 23.9 | 25.1 | 24.3 | 25.8 | 26.2 | 24.4 | 1.39 | 5.71 | 97.6 | 7 of 7 |
| 93 | 95.5 | 96 | 94.3 | 95.4 | 93.2 | 95.3 | 94.7 | 1.2 | 1.27 | 94.7 | 7 of 7 |
| 932 | 976 | 937 | 939 | 952 | 951 | 937 | 946 | 14.9 | 1.57 | 94.6 | 7 of 7 |
| 8940 | 9040 | 9000 | 9130 | 9110 | 8160* | 9180 | 9070 | 88.1 | 0.97 | 90.7 | 6 of 7 |
| Assay 2 | | | | | | | | | | | |
| 9.87 | 10.5 | 9.9 | 9.49 | 8.77 | 9.29 | 10 | 9.69 | 0.56 | 5.74 | 96.9 | 7 of 7 |
| 27.1 | 27.5 | 28.4 | 28 | 30.6* | 23.3 | 35.8* | 26.9 | 2.04 | 7.6 | 107 | 5 of 7 |
| 92.2 | 94.6 | 94.6 | 91.4 | 88.8 | 93.2 | 93.7 | 92.6 | 2.07 | 2.24 | 92.6 | 7 of 7 |
| 1040 | 1060 | 1070 | 1040 | 1040 | 1110 | 927 | 1040 | 55.9 | 5.37 | 104 | 7 of 7 |
| 9150 | 9210 | 8770 | 9120 | 8820 | 10300 | 10300 | 9390 | 660 | 7.04 | 93.9 | 7 of 7 |
| Assay 3 | | | | | | | | | | | |
| 10.9 | 9.37 | 9.25 | 9.5 | 7.62* | 9.13 | 9.8 | 9.66 | 0.66 | 6.84 | 96.6 | 6 of 7 |
| 25.2 | 24.9 | 25.2 | 26.1 | 24.5 | 25.6 | 25.8 | 25.3 | 0.56 | 2.2 | 101 | 7 of 7 |
| 101 | 101 | 101 | 102 | 96.6 | 101 | 107 | 101 | 2.91 | 2.88 | 101 | 7 of 7 |
| 1010 | 1010 | 965 | 995 | 977 | 1010 | 1030 | 1000 | 23.4 | 2.34 | 100 | 7 of 7 |
| 9870 | 9490 | 9780 | 9730 | 9810 | 9650 | 9700 | 9720 | 122 | 1.26 | 97.2 | 7 of 7 |

TABLE 8-continued

Intra- and inter-assay precision and accuracy of LSD

| Value #1 (pg/ml) | Value #2 (pg/ml) | Value #3 (pg/ml) | Value #4 (pg/ml) | Value #5 (pg/ml) | Value #6 (pg/ml) | Value #7 (pg/ml) | Mean (pg/ml) | SD (%) | CV (%) | Accuracy (%) | Num. Values |
|---|---|---|---|---|---|---|---|---|---|---|---|
| | | | | | | | | | | | |
| | | | | | Inter-assay 1-3 | | | | | | |
| | | | | | | | 9.6 | 0.694 | 7.23 | 96 | 19 of 21 |
| | | | | | | | 25.4 | 1.63 | 6.42 | 102 | 19 of 21 |
| | | | | | | | 96.2 | 4.26 | 4.43 | 96.2 | 21 of 21 |
| | | | | | | | 996 | 52.4 | 5.26 | 99.6 | 21 of 21 |
| | | | | | | | 9410 | 466 | 4.96 | 94.1 | 20 of 21 |

*out of the range of 85-115% (80-120% for LLOQ), not used for calculations

TABLE 9

Intra- and inter-assay precision and accuracy of O—H-LSD

| O—H-LSD Actual Concentration (pg/ml) | Value #1 (pg/ml) | Value #2 (pg/ml) | Value #3 (pg/ml) | Value #4 (pg/ml) | Value #5 (pg/ml) | Value #6 (pg/ml) | Value #7 (pg/ml) |
|---|---|---|---|---|---|---|---|
| | | | Assay 1 | | | | |
| 10 (LLOQ) | 9.53 | 8.6 | 9.59 | 7.96* | 9.25 | 11.4 | 10 |
| 25 (QC$_{LOW}$) | 24.5 | 20.5* | 22.5 | 24.9 | 25.9 | 25.5 | 24.6 |
| 100 (QC$_{MID}$) | 97.5 | 94 | 102 | 90.6 | 92.8 | 96.9 | 94.8 |
| 1000 (QC$_{HIGH}$) | 943 | 922 | 890 | 901 | 925 | 886 | 901 |
| 10000 (ULOQ) | 9050 | 8850 | 9010 | 9230 | 8970 | 8410* | 9070 |
| | | | Assay 2 | | | | |
| 10 (LLOQ) | 10.8 | 11.1 | 10.4 | 9.7 | 9.94 | 10.9 | 10 |
| 25 (QC$_{LOW}$) | 28 | 28.8 | 27.9 | 28.7 | 29.6* | 24.9 | 35.3* |
| 100 (QC$_{MID}$) | 96.2 | 91.1 | 95.7 | 87.8 | 88 | 97.7 | 96.6 |
| 1000 (QC$_{HIGH}$) | 1080 | 1020 | 1100 | 1090 | 1090 | 1120 | 921 |
| 10000 (ULOQ) | 8920 | 8810 | 8550 | 9250 | 8650 | 10300 | 10300 |
| | | | Assay 3 | | | | |
| 10 (LLOQ) | 9.78 | 11.6 | 10.8 | 11.3 | 10.2 | 8.85 | 12 |
| 25 (QC$_{LOW}$) | 25.1 | 27.1 | 25.7 | 29.1* | 26.9 | 27.3 | 25.2 |
| 100 (QC$_{MID}$) | 108 | 98.5 | 101 | 102 | 104 | 102 | 106 |
| 1000 (QC$_{HIGH}$) | 1030 | 1050 | 1030 | 1050 | 996 | 1050 | 990 |
| 10000 (ULOQ) | 10200 | 10100 | 10100 | 9850 | 9840 | 9770 | 10200 |
| | | | Inter-assay 1-3 | | | | |
| 10 (LLOQ) | | | | | | | |
| 25 (QC$_{LOW}$) | | | | | | | |
| 100 (QC$_{MID}$) | | | | | | | |
| 1000 (QC$_{HIGH}$) | | | | | | | |
| 10000 (ULOQ) | | | | | | | |

| O—H-LSD Actual Concentration (pg/ml) | Mean (pg/ml) | SD (%) | CV (%) | Accuracy (%) | Num. Values |
|---|---|---|---|---|---|
| | | Assay 1 | | | |
| 10 (LLOQ) | 9.74 | 0.96 | 9.84 | 97.4 | 6 of 7 |
| 25 (QC$_{LOW}$) | 24.7 | 1.18 | 4.77 | 98.6 | 6 of 7 |
| 100 (QC$_{MID}$) | 95.5 | 3.62 | 3.79 | 95.5 | 7 of 7 |
| 1000 (QC$_{HIGH}$) | 910 | 20.7 | 2.28 | 91 | 7 of 7 |
| 10000 (ULOQ) | 9030 | 124 | 1.37 | 90.3 | 6 of 7 |
| | | Assay 2 | | | |
| 10 (LLOQ) | 10.4 | 0.54 | 5.2 | 104 | 7 of 7 |
| 25 (QC$_{LOW}$) | 27.7 | 1.59 | 5.74 | 111 | 5 of 7 |
| 100 (QC$_{MID}$) | 93.3 | 4.23 | 4.53 | 93.3 | 7 of 7 |
| 1000 (QC$_{HIGH}$) | 1060 | 70.3 | 6.62 | 106 | 7 of 7 |
| 10000 (ULOQ) | 9250 | 748 | 8.08 | 92.6 | 7 of 7 |

TABLE 9-continued

Intra- and inter-assay precision and accuracy of O—H-LSD

| | Assay 3 | | | | |
|---|---|---|---|---|---|
| 10 (LLOQ) | 10.7 | 1.11 | 10.4 | 107 | 7 of 7 |
| 25 (QC$_{LOW}$) | 26.2 | 1.01 | 3.85 | 105 | 6 of 7 |
| 100 (QC$_{MID}$) | 103 | 3.23 | 3.14 | 103 | 7 of 7 |
| 1000 (QC$_{HIGH}$) | 1030 | 26.7 | 2.6 | 103 | 7 of 7 |
| 10000 (ULOQ) | 10000 | 181 | 1.81 | 100 | 7 of 7 |
| | Inter-assay 1-3 | | | | |
| 10 (LLOQ) | 10.3 | 0.933 | 9.07 | 103 | 20 of 21 |
| 25 (QC$_{LOW}$) | 26.1 | 1.72 | 6.59 | 104 | 17 of 21 |
| 100 (QC$_{MID}$) | 97.2 | 5.52 | 5.67 | 97.2 | 21 of 21 |
| 1000 (QC$_{HIGH}$) | 1000 | 79.3 | 7.93 | 100 | 21 of 21 |
| 10000 (ULOQ) | 9450 | 612 | 6.47 | 94.5 | 20 of 21 |

*out of the range of 85-115% (80-120% for LLOQ), not used for calculations

Selectivity

Selectivity I

Worked-up double Blank human plasma from seven different subjects did not show significant interference (≤12.1%) with the analytes (TABLE 10). Selectivity was evaluated also in presence of the deuterated ISTDs (Blank samples). The ISTDs did cause an insignificant interference for LSD (≤15.3%) and a minor for O-H-LSD (≤25.4%). Importantly, the observed interference was consistent in plasma from different subjects. Overall, the method was selective for the investigated analytes as shown in FIG. 4.

TABLE 10

Selectivity I of LSD, and O—H-LSD in human plasma

| | Plasma 1 | | Plasma 2 | | Plasma 3 | |
|---|---|---|---|---|---|---|
| LSD | Area (counts) | % of the LLOQ (%) | Area (counts) | % of the LLOQ (%) | Area (counts) | % of the LLOQ (%) |
| LLOQ | 7.61E+03 | — | 7.93E+03 | — | 8.10E+03 | — |
| Double Blank | 6.84E+02 | 9.00 | 3.87E+02 | 4.89 | 4.31E+02 | 5.32 |
| Blank | 6.72E+02 | 8.83 | 8.88E+02 | 11.2 | 9.07E+02 | 11.2 |

| | Plasma 4 | | Plasma 5 | | Plasma 6 | | Plasma 7 | |
|---|---|---|---|---|---|---|---|---|
| LSD | Area (counts) | % of the LLOQ (%) | Area (counts) | % of the LLOQ (%) | Area (counts) | % of the LLOQ (%) | Area (counts) | % of the LLOQ (%) |
| LLOQ | 8.03E+03 | — | 7.52E+03 | — | 8.03E+03 | — | 7.47E+03 | — |
| Double Blank | 3.66E+02 | 4.56 | 9.12E+02 | 12.1 | 4.71E+02 | 5.87 | 3.93E+02 | 5.26 |
| Blank | 1.01E+03 | 12.6 | 1.15E+03 | 15.3 | 8.56E+02 | 10.7 | 6.79E+02 | 9.09 |

| | Plasma 1 | | Plasma 2 | | Plasma 3 | |
|---|---|---|---|---|---|---|
| O—H-LSD | Area (counts) | % of the LLOQ (%) | Area (counts) | % of the LLOQ (%) | Area (counts) | % of the LLOQ (%) |
| LLOQ | 4.17E+03 | — | 4.31E+03 | — | 4.23E+03 | — |
| Double Blank | 8.28E+01 | 1.98 | 6.15E+01 | 1.43 | 1.03E+02 | 2.44 |
| Blank | 1.06E+03 | 25.4 | 9.63E+02 | 22.4 | 9.36E+02 | 22.1 |

| | Plasma 4 | | Plasma 5 | | Plasma 6 | | Plasma 7 | |
|---|---|---|---|---|---|---|---|---|
| O—H-LSD | Area (counts) | % of the LLOQ (%) | Area (counts) | % of the LLOQ (%) | Area (counts) | % of the LLOQ (%) | Area (counts) | % of the LLOQ (%) |
| LLOQ | 4.18E+03 | — | 4.10E+03 | — | 4.16E+03 | — | 3.99E+03 | — |
| Double Blank | 1.18E+02 | 2.82 | 8.46E+01 | 2.06 | 1.55E+02 | 3.73 | 5.43E+01 | 1.36 |
| Blank | 1.02E+03 | 24.4 | 9.04E+02 | 22.1 | 8.83E+02 | 21.2 | 8.26E+02 | 20.7 |

FIGS. 4A-4D show selectivity of LSD and O-H-LSD in human plasma. An overlay of seven O-H-LSD (FIG. 4A) and LSD (FIG. 4B) double Blank (thick black line) and LLOQ (dashed line) chromatograms is shown. An overlay of seven O-H-LSD (FIG. 4C) and LSD (FIG. 4D) blank (thick black line) and LLOQ (dashed line) chromatograms is shown. The interference of human plasma matrix is negligible in comparison to the lower limit of quantification (LLOQ) signal obtained for LSD and OH-LSD.

FIGS. 4A-4D show selectivity of LSD and O-H-LSD in human plasma. An overlay of seven O-H-LSD (FIG. 4A) and LSD (FIG. 4B) double Blank (grey) and LLOQ (turquoise) chromatograms is shown. An overlay of seven O-H-LSD (FIG. 4C) and LSD (FIG. 4D) Blank (grey) and LLOQ (turquoise) chromatograms is shown. The interference of human plasma matrix is negligible in comparison to the lower limit of quantification (LLOQ) signal obtained for LSD and OH-LSD.

Selectivity II

All the samples fulfill the selectivity II specifications (accuracy: 82.2-100%, precision of plasma 1-7: ≤6.29%), which underlines that the method is selective and sensitive to analyze LSD and O-H-LSD in plasma up to a concentration of 10 pg/ml. The results for LSD and O-H-LSD are presented in TABLE 11.

TABLE 11

Selectivity II of LSD, and O—H-LSD in human plasma

| LSD | Plasma 1 | Plasma 2 | Plasma 3 | Plasma 4 |
|---|---|---|---|---|
| Nominal concentration (pg/ml) | 10 | 10 | 10 | 10 |
| Found at (pg/ml) | 9.20 | 9.31 | 9.66 | 9.55 |
| SD (pg/ml) | 0.260 | 0.038 | 1.21 | 0.801 |
| CV (%) | 2.83 | 0.407 | 12.5 | 8.39 |
| Accuracy (%) | 92.0 | 93.1 | 96.6 | 95.5 |
| LSD | Plasma 5 | Plasma 6 | Plasma 7 | Plasma 1-7 |
| Nominal concentration (pg/ml) | 10 | 10 | 10 | 10 |
| Found at (pg/ml) | 8.39 | 9.48 | 8.58 | 9.17 |
| SD (pg/ml) | 0.662 | 0.241 | 0.540 | 0.493 |
| CV (%) | 7.89 | 2.55 | 6.29 | 5.38 |
| Accuracy (%) | 83.9 | 94.8 | 85.8 | 91.7 |
| O—H-LSD | Plasma 1 | Plasma 2 | Plasma 3 | Plasma 4 |
| Nominal concentration (pg/ml) | 10 | 10 | 10 | 10 |
| Found at (pg/ml) | 9.27 | 10.0 | 9.36 | 9.19 |
| SD (pg/ml) | 0.783 | 0.826 | 0.386 | 0.274 |
| CV (%) | 8.44 | 8.23 | 4.13 | 2.98 |
| Accuracy (%) | 92.7 | 100 | 93.6 | 91.9 |
| O—H-LSD | Plasma 5 | Plasma 6 | Plasma 7 | Plasma 1-7 |
| Nominal concentration (pg/ml) | 10 | 10 | 10 | 10 |
| Found at (pg/ml) | 8.22 | 9.09 | 8.62 | 9.11 |
| SD (pg/ml) | 0.257 | 0.291 | 0.471 | 0.574 |
| CV (%) | 3.12 | 3.20 | 5.47 | 6.29 |
| Accuracy (%) | 82.2 | 90.9 | 86.2 | 91.1 |

Carry-Over

The carry-over between two injections was ≤0.1%. Two double Blank samples were directly measured after the injection of an ULOQ sample. The mean signal intensity of second double Blank sample accounted for LSD and O-H-LSD on average for 19.6% and 14.7% of the signal at the LLOQ level, respectively (TABLE 12).

TABLE 12

Carry-over of LSD and O—H-LSD between different injections

| | | Assay 1 | | | Assay 2 | | | Assay 3 | |
|---|---|---|---|---|---|---|---|---|---|
| | Area, counts | Carry-over % LLOQ, % | Carry-over % ULOQ, % | Area, counts | Carry-over % LLOQ, % | Carry-over % ULOQ, % | Area, counts | Carry-over % LLOQ, % | Carry-over % ULOQ, % |
| LSD | | | | | | | | | |
| 1 LLOQ | 7.52E+03 | — | | 6.84E+03 | — | | 8.17E+03 | — | |
| 2 ULOQ | 6.41E+06 | — | | 6.21E+06 | | | 6.34E+06 | | |
| 3 1st Double blank after ULOQ | 7.31E+03 | 97.1 | 0.114 | 6.00E+03 | 87.6 | 0.097 | 5.03E+03 | 61.6 | 0.079 |
| 4 2nd Double blank after ULOQ | 1.40E+03 | 18.6 | 0.022 | 1.30E+03 | 19.0 | 0.021 | 1.73E+03 | 21.1 | 0.027 |
| O—H-LSD | | | | | | | | | |
| 1 LLOQ | 3.09E+03 | — | | 3.01E+03 | — | | 3.90E+03 | — | |
| 2 ULOQ | 2.77E+06 | | | 2.68E+06 | | | 2.80E+06 | | |
| 3 1st Double blank after ULOQ | 1.24E+03 | 40.1 | 0.045 | 1.72E+03 | 57.2 | 0.064 | 1.68E+03 | 43.1 | 0.060 |
| 4 2nd Double blank after ULOQ | 1.07E+02 | 3.46 | 0.004 | 6.31E+01 | 2.09 | 0.002 | 1.50E+03 | 38.5 | 0.054 |

Recovery

The overall recoveries for LSD and O-H-LSD are listed in TABLES 13 and 14, respectively. The recovery was consistent over the whole concentration range for all analytes and consistent between plasma originating from different subjects. A mean recovery of 98.3±1.35% and 102±3.84% was calculated for LSD and O-H-LSD, respectively. The recovery of the ISTD, LSD-$d_3$ and O-H-LSD-$d_{10}$, was similar compared to LSD and O-H-LSD.

TABLE 13

Recovery of LSD from human plasma of seven individuals

| | $QC_{Low}$: 25 pg/mL | | | $QC_{MID}$: 100 pg/mL | | |
|---|---|---|---|---|---|---|
| LSD | Before exctraction Peak Area (counts) | After exctraction Peak Area (counts) | Recovery (%) | Before exctraction Peak Area (counts) | After exctraction Peak Area (counts) | Recovery (%) |
| Plasma 1 | 1.80E+04 | 2.09E+04 | 86.1 | 6.88E+04 | 7.02E+04 | 98.0 |
| Plasma 2 | 1.88E+04 | 1.84E+04 | 102 | 6.99E+04 | 6.75E+04 | 104 |
| Plasma 3 | 1.94E+04 | 1.91E+04 | 102 | 7.01E+04 | 6.79E+04 | 103 |
| Plasma 4 | 1.83E+04 | 1.87E+04 | 97.9 | 6.88E+04 | 7.43E+04 | 92.6 |
| Plasma 5 | 1.93E+04 | 1.75E+04 | 110 | 6.97E+04 | 7.41E+04 | 94.1 |
| Plasma 6 | 1.83E+04 | 1.82E+04 | 101 | 6.85E+04 | 7.41E+04 | 92.4 |
| Plasma 7 | 1.78E+04 | 1.84E+04 | 96.7 | 6.84E+04 | 7.45E+04 | 91.8 |
| Plasma 1-7, Mean | 1.86E+04 | 1.87E+04 | 99.4 | 6.92E+04 | 7.18E+04 | 96.6 |
| Plasma 1-7, CV % | 3.36 | 5.70 | 7.29 | 1.02 | 4.42 | 5.36 |

| | $QC_{HIGH}$: 1000 pg/mL | | | ULOQ: 10000 pg/mL | | | LSD-$d_3$: 100 pg/mL | | |
|---|---|---|---|---|---|---|---|---|---|
| LSD | Before exctraction | After exctraction | Recovery | Before exctraction | After exctraction | Recovery | Before exctraction | After exctraction | Recovery |
| Plasma 1 | 6.77E+05 | 7.46E+05 | 90.8 | 6.89E+06 | 6.99E+06 | 98.6 | 2.06E+06 | 2.06E+06 | 100 |
| Plasma 2 | 6.99E+05 | 7.02E+05 | 100 | 6.93E+06 | 7.03E+06 | 98.6 | 2.01E+06 | 2.01E+06 | 100 |
| Plasma 3 | 7.31E+05 | 7.08E+05 | 103 | 6.97E+06 | 7.12E+06 | 97.9 | 2.05E+06 | 2.01E+06 | 102 |
| Plasma 4 | 7.14E+05 | 7.20E+05 | 99.2 | 6.77E+06 | 7.03E+06 | 96.3 | 2.07E+06 | 2.07E+06 | 100 |
| Plasma 5 | 7.17E+05 | 6.77E+05 | 106 | 6.85E+06 | 7.05E+06 | 97.2 | 2.05E+06 | 2.04E+06 | 100 |
| Plasma 6 | 7.31E+05 | 7.16E+05 | 102 | 7.18E+06 | 7.18E+06 | 100 | 2.08E+06 | 2.08E+06 | 100 |
| Plasma 7 | 6.81E+05 | 7.24E+05 | 94.1 | 6.72E+06 | 6.94E+06 | 96.8 | 2.00E+06 | 2.02E+06 | 99.2 |
| Plasma 1-7, Mean | 7.07E+05 | 7.13E+05 | 99.2 | 6.90E+06 | 7.05E+06 | 97.9 | 2.05E+06 | 2.04E+06 | 100 |
| Plasma 1-7, CV % | 3.13 | 2.98 | 5.29 | 2.18 | 1.13 | 1.30 | 1.44 | 1.48 | 0.858 |

TABLE 14

Recovery of O—H-LSD from human plasma of seven individuals

| | $QC_{Low}$: 25 pg/mL | | | $QC_{MID}$: 100 pg/mL | | |
|---|---|---|---|---|---|---|
| O—H-LSD | Before exctraction Peak Area (counts) | After exctraction Peak Area (counts) | Recovery (%) | Before exctraction Peak Area (counts) | After exctraction Peak Area (counts) | Recovery (%) |
| Plasma 1 | 8.01E+03 | 8.08E+03 | 99.1 | 3.08E+04 | 3.00E+04 | 103 |
| Plasma 2 | 8.52E+03 | 8.31E+03 | 103 | 3.22E+04 | 3.13E+04 | 103 |
| Plasma 3 | 8.61E+03 | 8.24E+03 | 104 | 3.11E+04 | 2.99E+04 | 104 |
| Plasma 4 | 8.30E+03 | 8.33E+03 | 100 | 3.19E+04 | 3.17E+04 | 101 |
| Plasma 5 | 8.85E+03 | 8.20E+03 | 108 | 3.10E+04 | 3.20E+04 | 96.9 |
| Plasma 6 | 8.65E+03 | 7.24E+03 | 119 | 2.98E+04 | 2.91E+04 | 102 |
| Plasma 7 | 9.35E+03 | 7.37E+03 | 127 | 3.12E+04 | 3.24E+04 | 96.3 |
| Plasma 1-7, Mean | 8.61E+03 | 7.97E+03 | 109 | 3.11E+04 | 3.09E+04 | 101 |
| Plasma 1-7, CV % | 4.91 | 5.79 | 9.74 | 2.50 | 4.03 | 3.05 |

| | $QC_{HIGH}$: 1000 pg/mL | | | ULOQ: 10000 pg/mL | | | O—H-LSD-$d_{10}$: 250 pg/mL | | |
|---|---|---|---|---|---|---|---|---|---|
| O—H-LSD | Before exctraction | After exctraction | Recovery | Before exctraction | After exctraction | Recovery | Before exctraction | After exctraction | Recovery |
| Plasma 1 | 2.93E+05 | 3.07E+05 | 95.4 | 2.91E+06 | 2.99E+06 | 97.3 | 2.19E+05 | 2.19E+05 | 100 |
| Plasma 2 | 3.16E+05 | 3.06E+05 | 103 | 3.09E+06 | 3.11E+06 | 99.4 | 2.32E+05 | 2.31E+05 | 101 |
| Plasma 3 | 3.30E+05 | 2.98E+05 | 111 | 3.07E+06 | 3.06E+06 | 100 | 2.26E+05 | 2.20E+05 | 103 |

TABLE 14-continued

Recovery of O—H-LSD from human plasma of seven individuals

| Plasma 4 | 3.09E+05 | 3.08E+05 | 100 | 2.91E+06 | 2.99E+06 | 97.3 | 2.27E+05 | 2.27E+05 | 100 |
|---|---|---|---|---|---|---|---|---|---|
| Plasma 5 | 3.25E+05 | 3.05E+05 | 107 | 3.09E+06 | 3.05E+06 | 101 | 2.30E+05 | 2.33E+05 | 98.7 |
| Plasma 6 | 3.07E+05 | 3.04E+05 | 101 | 3.05E+06 | 2.93E+06 | 104 | 2.26E+05 | 2.24E+05 | 101 |
| Plasma 7 | 3.08E+05 | 3.21E+05 | 96.0 | 2.98E+06 | 3.01E+06 | 99.0 | 2.29E+05 | 2.29E+05 | 100 |
| Plasma 1-7, Mean | 3.13E+05 | 3.07E+05 | 102 | 3.01E+06 | 3.02E+06 | 99.7 | 2.27E+05 | 2.26E+05 | 100 |
| Plasma 1-7, CV % | 3.96 | 2.27 | 5.54 | 2.67 | 1.94 | 2.33 | 1.91 | 2.36 | 1.38 |

Matrix effect

The Matrix effects of LSD and LSD-$d_3$ are illustrated in TABLE 15. The mean matrix effect of LSD was +8% and +18% for LSD-$d_3$. The matrix effect was consistent over different plasma lots (% CV ≤5.77%) and independent from the used LSD concentration (25-10000 pg/mL: ≤5.53%).

TABLE 15

Matrix effect of LSD and LSD-$d_3$ in human plasma of seven individuals

| LSD | QC$_{Low}$: 25 pg/mL | | QC$_{MID}$: 100 pg/mL | |
|---|---|---|---|---|
| | After extraction Peak Area (counts) | Matrix effect (%) | After extraction Peak Area (counts) | Matrix effect (%) |
| No Matrix | 1.61E+04 | — | 6.67E+04 | — |
| Plasma 1 | 2.09E+04 | 130 | 7.02E+04 | 105 |
| Plasma 2 | 1.84E+04 | 114 | 6.75E+04 | 101 |
| Plasma 3 | 1.91E+04 | 118 | 6.79E+04 | 102 |
| Plasma 4 | 1.87E+04 | 116 | 7.43E+04 | 111 |
| Plasma 5 | 1.75E+04 | 108 | 7.41E+04 | 111 |
| Plasma 6 | 1.82E+04 | 113 | 7.41E+04 | 111 |
| Plasma 7 | 1.84E+04 | 114 | 7.45E+04 | 112 |
| Plasma 1-7, Mean | 1.87E+04 | 116 | 7.18E+04 | 108 |
| Plasma 1-7, CV % | | 5.77 | | 4.38 |

| LSD | QC$_{HIGH}$: 1000 pg/mL | | ULOQ: 10000 pg/mL | | LSD-$d_3$: 100 pg/mL | |
|---|---|---|---|---|---|---|
| | After extraction Peak Area (counts) | Matrix effect (%) | After extraction Peak Area (counts) | Matrix effect (%) | After extraction Peak Area (counts) | Matrix effect (%) |
| No Matrix | 7.03E+05 | — | 6.49E+06 | — | 1.73E+06 | — |
| Plasma 1 | 7.46E+05 | 106 | 6.99E+06 | 108 | 2.06E+06 | 119 |
| Plasma 2 | 7.02E+05 | 100 | 7.03E+06 | 108 | 2.01E+06 | 116 |
| Plasma 3 | 7.08E+05 | 101 | 7.12E+06 | 110 | 2.01E+06 | 116 |
| Plasma 4 | 7.20E+05 | 102 | 7.03E+06 | 108 | 2.07E+06 | 119 |
| Plasma 5 | 6.77E+05 | 96.3 | 7.05E+06 | 109 | 2.04E+06 | 118 |
| Plasma 6 | 7.16E+05 | 102 | 7.18E+06 | 111 | 2.08E+06 | 120 |
| Plasma 7 | 7.24E+05 | 103 | 6.94E+06 | 107 | 2.02E+06 | 116 |
| Plasma 1-7, Mean | 7.13E+05 | 101 | 7.05E+06 | 109 | 2.04E+06 | 118 |
| Plasma 1-7, CV % | | 2.98 | | 1.12 | | 1.48 |

The Matrix effects of O-H-LSD and O-H-LSD-d10 are depict in TABLE 16. The mean matrix effect of LSD was −10% and −6.8% for O-H-LSD-$d_{10}$. The matrix effect was consistent over different plasma lots (% CV ≤5.77%) and independent from the employed O-H-LSD concentration (CV % 25-10000 pg/mL: ≤2.65%).

TABLE 16

Matrix effect of O—H-LSD and O—H-LSD-$d_{10}$ in human plasma of seven individuals

| O—H-LSD | $QC_{Low}$: 25 pg/mL | | $QC_{MID}$: 100 pg/mL | |
|---|---|---|---|---|
| | After extraction Peak Area (counts) | Matrix effect (%) | After extraction Peak Area (counts) | Matrix effect (%) |
| No Matrix | 8.95E+03 | — | 3.47E+04 | — |
| Plasma 1 | 8.08E+03 | 90.3 | 3.00E+04 | 86.6 |
| Plasma 2 | 8.31E+03 | 92.9 | 3.13E+04 | 90.3 |
| Plasma 3 | 8.24E+03 | 92.1 | 2.99E+04 | 86.3 |
| Plasma 4 | 8.33E+03 | 93.1 | 3.17E+04 | 91.3 |
| Plasma 5 | 8.20E+03 | 91.7 | 3.20E+04 | 92.3 |
| Plasma 6 | 7.24E+03 | 81.0 | 2.91E+04 | 84.0 |
| Plasma 7 | 7.37E+03 | 82.4 | 3.24E+04 | 93.4 |
| Plasma 1-7, Mean | 7.97E+03 | 89.1 | 3.09E+04 | 89.2 |
| Plasma 1-7, CV % | | 5.77 | | 3.98 |

| O—H-LSD | $QC_{HIGH}$: 1000 pg/mL | | ULOQ: 10000 pg/mL | | O—H-LSD-$d_{10}$: 250 pg/mL | |
|---|---|---|---|---|---|---|
| | After extraction Peak Area (counts) | Matrix effect (%) | After extraction Peak Area (counts) | Matrix effect (%) | After extraction Peak Area (counts) | Matrix effect (%) |
| No Matrix | 3.50E+05 | — | 3.24E+06 | — | 2.43E+05 | — |
| Plasma 1 | 3.07E+05 | 87.5 | 2.99E+06 | 92.1 | 2.19E+05 | 90.3 |
| Plasma 2 | 3.06E+05 | 87.4 | 3.11E+06 | 95.9 | 2.31E+05 | 95.2 |
| Plasma 3 | 2.98E+05 | 85.0 | 3.06E+06 | 94.3 | 2.20E+05 | 90.8 |
| Plasma 4 | 3.08E+05 | 87.8 | 2.99E+06 | 92.2 | 2.27E+05 | 93.5 |
| Plasma 5 | 3.05E+05 | 87.1 | 3.05E+06 | 94.2 | 2.33E+05 | 96.1 |
| Plasma 6 | 3.04E+05 | 86.6 | 2.93E+06 | 90.2 | 2.24E+05 | 92.2 |
| Plasma 7 | 3.21E+05 | 91.5 | 3.01E+06 | 92.8 | 2.29E+05 | 94.5 |
| Plasma 1-7, Mean | 3.07E+05 | 87.6 | 3.02E+06 | 93.1 | 2.26E+05 | 93.2 |
| Plasma 1-7, CV % | | 2.27 | | 1.99 | | 2.36 |

Stability Tests

Reinjection Reproducibility

The validation run and its reinjection were valid. This shows that a run can be re-injected after overnight storage at 10° C. in the autosampler and for at least one week at −20° C. in the case of failure of the LC-MS/MS system. The deviations of the means of the QCs of the two runs after overnight storage at 10° C. were between −0.451% to +2.3% for LSD and between −1.59% to +2.08% for O-H-LSD. The reinjected QC samples fulfilled the specification criteria for a validation run. The results are presented in TABLES 17 and 18. The deviations of the means of the QCs of the two runs after 8 days at −20° C. were between −1.85% to +1.02% for LSD and between −2.09% to +1.9% for O-H-LSD. The reinjected QC samples fulfilled the specification criteria for a validation run. The results are presented in TABLES 19 and 20.

TABLE 17

QC results for LSD from reinjection following overnight storage at 10° C. in the autosampler.

| LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| | No | | | | | | | | | | |
| Baseline | | | | | | | | | | | |
| | 1 | 9.82 | 98.2 | 23.3 | 93 | 93 | 93 | 932 | 93.2 | 8940 | 89.4 |
| | 2 | 10.5 | 105 | 22.3 | 89 | 95.5 | 95.5 | 976 | 97.6 | 9040 | 90.4 |
| | 3 | 10.5 | 105 | 23.9 | 95.7 | 96 | 96 | 937 | 93.7 | 9000 | 90.1 |
| | 4 | 9.08 | 90.8 | 25.1 | 100 | 94.3 | 94.3 | 939 | 93.9 | 9130 | 91.3 |
| | 5 | 8.65 | 86.5 | 24.3 | 97.3 | 95.4 | 95.4 | 952 | 95.2 | 9110 | 91.1 |
| | 6 | 8.15 | 81.5 | 25.8 | 103 | 93.2 | 93.2 | 951 | 95.1 | 8160* | 81.6* |
| | 7 | 9.45 | 94.5 | 26.2 | 105 | 95.3 | 95.3 | 937 | 93.7 | 9180 | 91.8 |
| Intra-assay | Mean | 9.45 | 94.5 | 24.4 | 97.6 | 94.7 | 94.7 | 946 | 94.6 | 9070 | 90.7 |
| | SD | 0.899 | | 1.4 | | 1.2 | | 14.9 | | 89.4 | |
| | CV % | 9.51 | | 5.72 | | 1.27 | | 1.57 | | 0.986 | |
| | N | 7 | | 7 | | 7 | | 7 | | 6 | |
| 1 night at 10° C. | | | | | | | | | | | |
| | 1 | 10.3 | 103 | 23.2 | 92.9 | 97 | 97 | 941 | 94.1 | 9100 | 91 |
| | 2 | 9.8 | 98 | 20.9* | 83.5* | 98.6 | 98.6 | 926 | 92.6 | 9020 | 90.2 |
| | 3 | 9.17 | 91.8 | 24.4 | 97.5 | 96.2 | 96.2 | 958 | 95.8 | 8950 | 89.5 |
| | 4 | 9.04 | 90.4 | 24.4 | 97.7 | 95.6 | 95.6 | 954 | 95.4 | 9040 | 90.4 |
| | 5 | 9.42 | 94.2 | 25.2 | 101 | 97.5 | 97.5 | 946 | 94.6 | 9270 | 92.7 |
| | 6 | 9.49 | 94.9 | 25.3 | 101 | 95.5 | 95.5 | 941 | 94.1 | 8240* | 82.4* |
| | 7 | 9.68 | 96.8 | 23.9 | 95.4 | 97.4 | 97.4 | 928 | 92.8 | 9230 | 92.3 |
| Intra-assay | Mean | 9.56 | 95.6 | 24.4 | 97.6 | 96.8 | 96.8 | 942 | 94.2 | 9100 | 91 |
| | SD | 0.419 | | 0.795 | | 1.13 | | 12.3 | | 125 | |
| | CV % | 4.38 | | 3.26 | | 1.17 | | 1.3 | | 1.38 | |
| | N | 7 | | 6 | | 7 | | 7 | | 6 | |
| Change in concentration [%] | | 1.09 | | −0.0195 | | 2.3 | | −0.451 | | 0.383 | |

TABLE 18

QC results for O—H-LSD from reinjection following overnight storage at 10° C. in the autosampler.

| O—H-LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| | No | | | | | | | | | | |
| Baseline | | | | | | | | | | | |
| | 1 | 9.53 | 95.3 | 24.5 | 97.9 | 97.5 | 97.5 | 943 | 94.3 | 9050 | 90.5 |
| | 2 | 8.6 | 86 | 20.5* | 81.9* | 94 | 94 | 922 | 92.2 | 8850 | 88.5 |
| | 3 | 9.59 | 95.9 | 22.5 | 90 | 102 | 102 | 890 | 89 | 9010 | 90.1 |
| | 4 | 7.96* | 79.6* | 24.9 | 99.8 | 90.6 | 90.6 | 901 | 90.1 | 9230 | 92.3 |
| | 5 | 9.25 | 92.5 | 25.9 | 103 | 92.8 | 92.8 | 925 | 92.5 | 8970 | 89.7 |
| | 6 | 11.4 | 114 | 25.5 | 102 | 96.9 | 96.9 | 886 | 88.6 | 8410* | 84.1* |
| | 7 | 10 | 100 | 24.6 | 98.5 | 94.8 | 94.8 | 901 | 90.1 | 9070 | 90.7 |
| Intra-assay | Mean | 9.74 | 97.4 | 24.6 | 98.6 | 95.5 | 95.5 | 910 | 91 | 9030 | 90.3 |
| | SD | 1.0 | | 1.17 | | 3.62 | | 20.7 | | 124 | |
| | CV % | 9.83 | | 4.77 | | 3.79 | | 2.28 | | 1.37 | |
| | N | 6 | | 6 | | 7 | | 7 | | 6 | |
| 1 night at 10° C. | | | | | | | | | | | |
| | 1 | 9.97 | 99.7 | 22.9 | 91.7 | 93.4 | 93.4 | 953 | 95.3 | 9030 | 90.3 |
| | 2 | 10.5 | 105 | 23.3 | 93 | 94.2 | 94.2 | 951 | 95.1 | 9110 | 91.1 |
| | 3 | 10.1 | 101 | 25.2 | 101 | 101 | 101 | 896 | 89.6 | 8920 | 89.2 |
| | 4 | 10.6 | 106 | 25.5 | 102 | 94.8 | 94.8 | 932 | 93.2 | 9120 | 91.2 |
| | 5 | 9.26 | 92.6 | 26.5 | 106 | 92.3 | 92.3 | 933 | 93.3 | 8950 | 89.6 |
| | 6 | 10.4 | 104 | 24.5 | 98.1 | 92 | 92 | 919 | 91.9 | 8330* | 83.3* |
| | 7 | 8.6 | 86 | 24.3 | 97.2 | 89.7 | 89.7 | 917 | 91.7 | 9090 | 90.9 |

TABLE 18-continued

QC results for O—H-LSD from reinjection following overnight storage at 10° C. in the autosampler.

| O—H-LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Intra-assay | Mean | 9.92 | 99.2 | 24.6 | 98.4 | 94 | 94 | 929 | 92.9 | 9040 | 90.4 |
| | SD | 0.737 | | 1.27 | | 3.61 | | 20 | | 84.8 | |
| | CV % | 7.43 | | 5.16 | | 3.84 | | 2.16 | | 0.938 | |
| | N | 7 | | 7 | | 7 | | 7 | | 6 | |
| Change in concentration [%] | | 1.86 | | −0.149 | | −1.59 | | 2.08 | | 0.101 | |

TABLE 19

QC results for LSD from reinjection following 8 days storage at −20° C.

| LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 10.9 | 109 | 25.2 | 101 | 101 | 101 | 1010 | 101 | 9870 | 98.7 |
| | 2 | 9.37 | 93.7 | 24.9 | 99.5 | 101 | 101 | 1010 | 101 | 9490 | 95 |
| | 3 | 9.25 | 92.5 | 25.2 | 101 | 101 | 101 | 965 | 96.5 | 9780 | 97.9 |
| | 4 | 9.5 | 95 | 26.1 | 104 | 102 | 102 | 995 | 99.5 | 9730 | 97.3 |
| | 5 | 7.62* | 76.3* | 24.5 | 97.9 | 96.6 | 96.6 | 977 | 97.7 | 9810 | 98.1 |
| | 6 | 9.13 | 91.3 | 25.6 | 102 | 101 | 101 | 1010 | 101 | 9650 | 96.5 |
| | 7 | 9.8 | 98 | 25.8 | 103 | 107 | 107 | 1030 | 103 | 9700 | 97.1 |
| Intra-assay | Mean | 9.66 | 96.6 | 25.3 | 101 | 101 | 101 | 1000 | 100 | 9720 | 97.2 |
| | SD | 0.662 | | 0.557 | | 2.91 | | 23.4 | | 122 | |
| | CV % | 6.85 | | 2.2 | | 2.88 | | 2.34 | | 1.26 | |
| | N | 6 | | 7 | | 7 | | 7 | | 7 | |
| 8 days at −20° C. | | | | | | | | | | | |
| | 1 | 10.4 | 104 | 23.9 | 95.5 | 101 | 101 | 1010 | 101 | 9740 | 97.4 |
| | 2 | 9.75 | 97.5 | 25.6 | 102 | 103 | 103 | 988 | 98.8 | 9660 | 96.6 |
| | 3 | 8.6 | 86 | 26.6 | 107 | 102 | 102 | 989 | 98.9 | 9520 | 95.2 |
| | 4 | 9.53 | 95.3 | 24.1 | 96.4 | 102 | 102 | 999 | 99.9 | 9290 | 92.9 |
| | 5 | 10 | 100 | 26.5 | 106 | 103 | 103 | 991 | 99.1 | 9510 | 95.1 |
| | 6 | 9.47 | 94.7 | 23 | 92 | 99.9 | 99.9 | 1010 | 101 | 9640 | 96.4 |
| | 7 | 9.03 | 90.3 | 25.9 | 103 | 105 | 105 | 996 | 99.6 | 9420 | 94.2 |
| Intra-assay | Mean | 9.54 | 95.4 | 25.1 | 100 | 102 | 102 | 997 | 99.7 | 9540 | 95.4 |
| | SD | 0.599 | | 1.42 | | 1.44 | | 9.35 | | 152.00 | |
| | CV % | 6.28 | | 5.65 | | 1.41 | | 0.938 | | 1.59 | |
| | N | 7 | | 7 | | 7 | | 7 | | 7 | |
| Change in concentration [%] | | −1.26 | | −0.948 | | 1.02 | | −0.333 | | −1.85 | |

TABLE 20

QC results for O—H-LSD from reinjection following 8 days storage at −20° C.

| O—H-LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 9.78 | 97.8 | 25.1 | 100 | 108 | 108 | 1030 | 103 | 10200 | 102 |
| | 2 | 11.6 | 116 | 27.1 | 108 | 98.5 | 98.5 | 1050 | 106 | 10100 | 101 |
| | 3 | 10.8 | 108 | 25.7 | 103 | 101 | 101 | 1030 | 103 | 10100 | 101 |
| | 4 | 11.3 | 113 | 29.1* | 116* | 102 | 102 | 1050 | 105 | 9850 | 98.5 |

TABLE 20-continued

QC results for O—H-LSD from reinjection following 8 days storage at −20° C.

| O—H-LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| | 5 | 10.2 | 102 | 26.9 | 108 | 104 | 104 | 996 | 99.6 | 9840 | 98.4 |
| | 6 | 8.85 | 88.5 | 27.3 | 109 | 102 | 102 | 1050 | 105 | 9770 | 97.7 |
| | 7 | 12 | 120 | 25.2 | 101 | 106 | 106 | 990 | 99 | 10200 | 102 |
| Intra-assay | Mean | 10.7 | 107 | 26.2 | 105 | 103 | 103 | 1030 | 103 | 10000 | 100 |
| | SD | 1.11 | | 1.01 | | 3.23 | | 26.7 | | 181 | |
| | CV % | 10.4 | | 3.84 | | 3.14 | | 2.6 | | 1.81 | |
| | N | 7 | | 6 | | 7 | | 7 | | 7 | |
| 8 days at −20° C. | | | | | | | | | | | |
| | 1 | 9.95 | 99.5 | 25.9 | 104 | 109 | 109 | 1010 | 101 | 9730 | 97.3 |
| | 2 | 10.6 | 106 | 28.7 | 115 | 98 | 98 | 1050 | 105 | 9760 | 97.6 |
| | 3 | 11.6 | 116 | 27.1 | 109 | 104 | 104 | 1010 | 101 | 9750 | 97.5 |
| | 4 | 10.7 | 107 | 24.1 | 96.5 | 109 | 109 | 993 | 99.3 | 9690 | 96.9 |
| | 5 | 9.42 | 94.2 | 25.9 | 104 | 106 | 106 | 1000 | 100 | 10300 | 103 |
| | 6 | 9.39 | 93.9 | 26.9 | 108 | 102 | 102 | 1020 | 102 | 9880 | 98.8 |
| | 7 | 11.3 | 113 | 24.3 | 97.3 | 107 | 107 | 1040 | 104 | 10100 | 101 |
| Intra-assay | Mean | 10.4 | 104 | 26.1 | 105 | 105 | 105 | 1020 | 102 | 9880 | 98.8 |
| | SD | 0.883 | | 1.61 | | 3.86 | | 22.5 | | 211 | |
| | CV % | 8.46 | | 6.16 | | 3.68 | | 2.21 | | 2.13 | |
| | N | 7 | | 7 | | 7 | | 7 | | 7 | |
| Change in concentration [%] | | −2.09 | | −0.294 | | 1.9 | | −1.05 | | −1.27 | |

Freeze/Thaw and Short-Term Stability

LSD and O-H-LSD did not show a significant change in plasma concentration after three freeze/thaw cycles and height hours at room temperature (TABLES 21-24). Change in plasma concentration was ≤8.83% for LSD and ≤6.46% for O-H-LSD following three freeze/thaw cycles. After 8 hours storage at room temperature, the LSD and O-H-LSD change in plasma concentration was ≤3.81% and ≤4.52%, respectively.

TABLE 21

LSD stability following three freeze-thaw cycles

| LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 9.57 | 95.7 | 23.3 | 93.4 | 94.3 | 94.3 | 964 | 96.4 | 9490 | 94.9 |
| | 2 | 8.32 | 83.2 | 22.6 | 90.5 | 97.4 | 97.4 | 943 | 94.3 | 10000 | 100 |
| | 3 | 9.66 | 96.6 | 23.5 | 94 | 101 | 101 | 969 | 96.9 | 9470 | 94.7 |
| | 4 | | | | | | | | | | |
| | 5 | | | | | | | | | | |
| | 6 | | | | | | | | | | |
| | 7 | | | | | | | | | | |
| Intra-assay | Mean | 9.18 | 91.8 | 23.1 | 92.6 | 97.5 | 97.5 | 959 | 95.9 | 9660 | 96.6 |
| | SD | 0.749 | | 0.471 | | 3.23 | | 13.6 | | 308 | |
| | CV % | 8.16 | | 2.03 | | 3.31 | | 1.42 | | 3.19 | |
| | N | 3 | | 3 | | 3 | | 3 | | 3 | |
| 3 F/T cycles | | | | | | | | | | | |
| | 1 | 8.19 | 81.9 | 23.8 | 95.2 | 99.2 | 99.2 | 964 | 96.4 | 9780 | 97.8 |
| | 2 | 7.5* | 75.0* | 25.5 | 102 | 97.9 | 97.9 | 962 | 96.2 | 9430 | 94.3 |
| | 3 | 8.17 | 81.7 | 25.2 | 101 | 99.5 | 99.5 | 969 | 96.9 | 9400 | 94 |
| | 4 | 8.47 | 84.7 | 22.9 | 91.5 | 99.6 | 99.6 | 967 | 96.7 | 9640 | 96.4 |
| | 5 | 7.97* | 79.8* | 24.7 | 98.8 | 94.9 | 94.9 | 946 | 94.6 | 9920 | 99.2 |
| | 6 | 8.18 | 81.8 | 23.4 | 93.6 | 98 | 98 | 962 | 96.2 | 9300 | 93 |
| | 7 | 8.85 | 88.5 | 23.7 | 94.9 | 100 | 100 | 983 | 98.3 | 9520 | 95.2 |
| Intra-assay | Mean | 8.37 | 83.7 | 24.2 | 96.7 | 98.5 | 98.5 | 965 | 96.5 | 9570 | 95.7 |
| | SD | 0.295 | | 0.968 | | 1.78 | | 10.9 | | 221.00 | |
| | CV % | 3.53 | | 4 | | 1.81 | | 1.13 | | 2.31 | |
| | N | 5 | | 7 | | 7 | | 7 | | 7 | |
| Change in concentration [%] | | −8.83 | | 4.44 | | 1.03 | | 0.647 | | −0.9 | |

TABLE 22

O—H-LSD stability following three freeze-thaw cycles

| O—H-LSD | | LLOQ: 10 pg/ml | | QC$_{LOW}$: 25 pg/ml | | QC$_{MID}$: 100 pg/ml | | QC$_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 8.89 | 88.9 | 22.9 | 91.5 | 98.6 | 98.6 | 962 | 96.2 | 9230 | 92.3 |
| | 2 | 8.94 | 89.4 | 25 | 99.8 | 91.4 | 91.4 | 959 | 95.9 | 9970 | 99.7 |
| | 3 | 9.5 | 95 | 23.7 | 94.7 | 95.7 | 95.7 | 977 | 97.7 | 9420 | 94.2 |
| | 4 | | | | | | | | | | |
| | 5 | | | | | | | | | | |
| | 6 | | | | | | | | | | |
| | 7 | | | | | | | | | | |
| Intra-assay | Mean | 9.11 | 91.1 | 23.8 | 95.3 | 95.2 | 95.2 | 966 | 96.6 | 9540 | 95.4 |
| | SD | 0.339 | | 1.04 | | 3.62 | | 9.97 | | 386 | |
| | CV % | 3.72 | | 4.38 | | 3.8 | | 1.03 | | 4.04 | |
| | N | 3 | | 3 | | 3 | | 3 | | 3 | |
| 3 F/T cycles | | | | | | | | | | | |
| | 1 | 9.59 | 95.9 | 27.3 | 109 | 95.4 | 95.4 | 950 | 95 | 9290 | 92.9 |
| | 2 | 9.71 | 97.1 | 24.2 | 96.6 | 102 | 102 | 931 | 93.1 | 9260 | 92.6 |
| | 3 | 8.17 | 81.7 | 22.9 | 91.4 | 98.9 | 98.9 | 975 | 97.5 | 9620 | 96.2 |
| | 4 | 9.52 | 95.2 | 25.3 | 101 | 100 | 100 | 962 | 96.2 | 9600 | 96 |
| | 5 | 10.8 | 108 | 24.4 | 97.5 | 102 | 102 | 995 | 99.5 | 9480 | 94.8 |
| | 6 | 10.4 | 104 | 22.3 | 89.3 | 94.8 | 94.8 | 977 | 97.7 | 9440 | 94.4 |
| | 7 | 7.39* | 73.9* | 23.2 | 92.9 | 97.3 | 97.3 | 981 | 98.1 | 9720 | 97.2 |
| Intra-assay | Mean | 9.7 | 97 | 24.2 | 96.9 | 98.7 | 98.7 | 967 | 96.7 | 9490 | 94.9 |
| | SD | 0.908 | | 1.68 | | 3.05 | | 21.4 | | 173.00 | |
| | CV % | 9.36 | | 6.95 | | 3.08 | | 2.21 | | 1.83 | |
| | N | 6 | | 7 | | 7 | | 7 | | 7 | |
| Change in concentration [%] | | 6.46 | | 1.57 | | 3.7 | | 0.123 | | −0.589 | |

TABLE 23

LSD stability following 8 hours storage at room temperature

| LSD | | LLOQ: 10 pg/ml | | QC$_{LOW}$: 25 pg/ml | | QC$_{MID}$: 100 pg/ml | | QC$_{HIGH}$: 1000 pg/ml | | QC$_{ULOQ}$: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 9.57 | 95.7 | 23.3 | 93.4 | 94.3 | 94.3 | 964 | 96.4 | 9490 | 94.9 |
| | 2 | 8.32 | 83.2 | 22.6 | 90.5 | 97.4 | 97.4 | 943 | 94.3 | 10000 | 100 |
| | 3 | 9.66 | 96.6 | 23.5 | 94 | 101 | 101 | 969 | 96.9 | 9470 | 94.7 |
| | 4 | | | | | | | | | | |
| | 5 | | | | | | | | | | |
| | 6 | | | | | | | | | | |
| | 7 | | | | | | | | | | |
| Intra-assay | Mean | 9.18 | 91.8 | 23.1 | 92.6 | 97.5 | 97.5 | 959 | 95.9 | 9660 | 96.6 |
| | SD | 0.749 | | 0.471 | | 3.23 | | 13.6 | | 308 | |
| | CV % | 8.16 | | 2.03 | | 3.31 | | 1.42 | | 3.19 | |
| | N | 3 | | 3 | | 3 | | 3 | | 3 | |
| 8 h at RT | | | | | | | | | | | |
| | 1 | 9.16 | 91.6 | 24 | 96 | 95.9 | 95.9 | 982 | 98.2 | 9460 | 94.7 |
| | 2 | 8.56 | 85.6 | 23.2 | 92.9 | 95.8 | 95.8 | 983 | 98.3 | 9340 | 93.4 |
| | 3 | 7.47* | 74.7* | 23.6 | 94.5 | 94.2 | 94.2 | 972 | 97.2 | 9460 | 94.6 |
| | 4 | 8.3 | 83.10 | 21.9 | 87.6 | 91.1 | 91.1 | 968 | 96.8 | 9690 | 96.9 |
| | 5 | 9.2 | 92 | 23.6 | 94.4 | 99.2 | 99.2 | 962 | 96.2 | 9540 | 95.4 |
| | 6 | 8.61 | 86.1 | 23.3 | 93.3 | 99.7 | 99.7 | 977 | 97.7 | 9500 | 95 |
| | 7 | 9.17 | 91.7 | 22.5 | 90 | 95.9 | 95.9 | 1000 | 100 | 9430 | 94.3 |
| Intra-assay | Mean | 8.83 | 88.3 | 23.2 | 92.7 | 96 | 96 | 978 | 97.8 | 9490 | 94.9 |
| | SD | 0.391 | | 0.728 | | 2.92 | | 12.4 | | 110.00 | |
| | CV % | 4.42 | | 3.14 | | 3.04 | | 1.27 | | 1.16 | |
| | N | 6 | | 7 | | 7 | | 7 | | 7 | |
| Change in concentration [%] | | 3.81 | | 0.0885 | | −1.51 | | 1.99 | | −1.74 | |

TABLE 24

O—H-LSD stability following 8 hours storage at room temperature

| O—H-LSD | | LLOQ: 10 pg/ml | | QCLOW: 25 pg/ml | | $QC_{MID}$: 100 pg/ml | | $QC_{HIGH}$: 1000 pg/ml | | ULOQ: 10000 pg/ml | |
|---|---|---|---|---|---|---|---|---|---|---|---|
| | No | Found at [ng/ml] | Accuracy [%] | Found at [ng/ml] | Accuracy [%] | Found at [ng/ml] | Accuracy [%] | Found at [ng/ml] | Accuracy [%] | Found at [ng/ml] | Accuracy [%] |
| Baseline | | | | | | | | | | | |
| | 1 | 8.89 | 88.9 | 22.9 | 91.5 | 98.6 | 98.6 | 962 | 96.2 | 9230 | 92.3 |
| | 2 | 8.94 | 89.4 | 25 | 99.8 | 91.4 | 91.4 | 959 | 95.9 | 9970 | 99.7 |
| | 3 | 9.5 | 95 | 23.7 | 94.7 | 95.7 | 95.7 | 977 | 97.7 | 9420 | 94.2 |
| | 4 | | | | | | | | | | |
| | 5 | | | | | | | | | | |
| | 6 | | | | | | | | | | |
| | 7 | | | | | | | | | | |
| Intra-assay | Mean | 9.11 | 91.1 | 23.8 | 95.3 | 95.2 | 95.2 | 966 | 96.6 | 9540 | 95.4 |
| | SD | 0.339 | | 1.04 | | 3.62 | | 9.97 | | 386 | |
| | CV % | 3.72 | | 4.38 | | 3.8 | | 1.03 | | 4.04 | |
| | N | 3 | | 3 | | 3 | | 3 | | 3 | |
| 8 h at RT | | | | | | | | | | | |
| | 1 | 9.04 | 90.4 | 22.3 | 89.2 | 97.1 | 97.1 | 960 | 96 | 9020 | 90.2 |
| | 2 | 9.43 | 94.3 | 23.3 | 93.3 | 91.5 | 91.5 | 1000 | 100 | 9300 | 93 |
| | 3 | 6.38* | 63.8* | 24.4 | 97.6 | 95.2 | 95.2 | 918 | 91.8 | 9070 | 90.7 |
| | 4 | 7.75* | 77.5* | 25.6 | 102 | 98.3 | 98.3 | 946 | 94.6 | 8820 | 88.2 |
| | 5 | 8.31 | 83.1 | 25.9 | 103 | 94.6 | 94.6 | 936 | 93.6 | 9320 | 93.2 |
| | 6 | 10.1 | 101 | 24.3 | 97.1 | 99.6 | 99.6 | 958 | 95.8 | 9150 | 91.5 |
| | 7 | 8.79 | 87.9 | 23 | 91.9 | 94.5 | 94.5 | 939 | 93.9 | 9110 | 91.1 |
| Intra-assay | Mean | 9.13 | 91.2 | 24.1 | 96.4 | 95.8 | 95.8 | 951 | 95.1 | 9110 | 91.1 |
| | SD | 0.662 | | 1.32 | | 2.72 | | 27 | | 170.00 | |
| | CV % | 7.25 | | 5.47 | | 2.84 | | 2.84 | | 1.86 | |
| | N | 5 | | 7 | | 7 | | 7 | | 7 | |
| Change in concentration [%] | | 0.176 | | 1.1 | | 0.652 | | -1.51 | | -4.52 | |

Clinical Application of the LC-MS/MS Method

Figure 5:
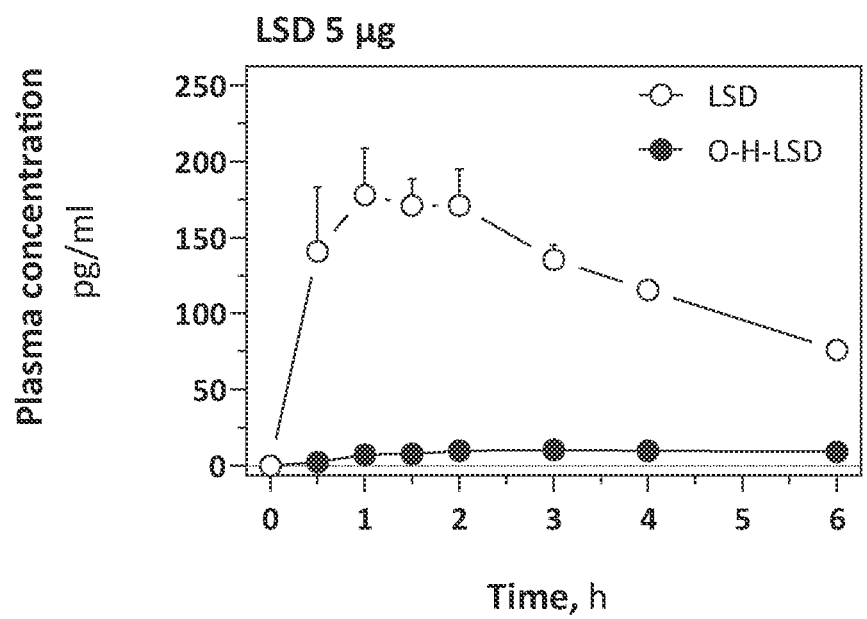
FIG. 5 is a graph showing that the pharmacokinetics of three healthy volunteers receiving an oral dose of 5 µg LSD can be established with the developed method.

The application of the method was assessed by analyzing the PK of LSD and O-H-LSD in three healthy volunteers treated with an oral dose of 5 µg LSD base (FIG. 5). An oral dose of 5 µg LSD base in ethanol (Holze et al., 2021) was administered to three healthy volunteers. Plasma concentrations of LSD and O-H-LSD were quantified before and up to six hours post-treatment. FIG. 5 shows the concentration-time profile of LSD and O-H-LSD. Mean values and the standard deviations are illustrated.

The maximal plasma level of LSD and O-H-LSD was on average 178 pg/ml (SD: 30.6 pg/ml) and 10.4 pg/ml (SD: 2.59 pg/ml), respectively. LSD reached $T_{max}$ approximately after 1 hour post-treatment, whereas O-H-LSD peaked after 3 hours. The LSD concentrations measured after a dose of only 5 µg were approximately 7 to 18 times higher than the methods limit of quantification. Thus, the PK of LSD could straightforwardly be established also for very low so-called microdoses (Kuypers et al., 2019). In the case of O-H-LSD, a larger amount of plasma sample was required to determine the plasma concentration time profile after a dose of 5 µg. Three times more plasma was utilized (150 instead of 50 µl), which was extracted as outlined above using however three-fold more acetonitrile for the extraction. Sensitivity was increased by evaporating the extract and reconstituting the residue in a mixture of 150 µl of mobile phase A and mobile phase B (9/1 v/v). This example shows that the sensitivity of the method can simply be improved by using a larger amount of sample. In future, it will also be considered to inject a larger amount of extract, which is in a first step retained and concentrated on a trapping column. In a second step, the direction of the flow is inverted and so that the sample can be loaded and eluted on the analytical column. This column switching procedure, will increase the sensitivity in the event that the sample can be retained on the trap column. Importantly, the time-consuming solvent evaporation step can thereby be avoided.

Overall, the method application example demonstrates that the method is suitable for quantification of the clinical samples using LSD microdoses. Moreover, the method can readily be adapted if the sensitivity of the analysis has to be improved.

CONCLUSION

Compared to other bioanalytical methods that measure LSD in human plasma, the method described herein required only small amounts of sample and featured a straightforward extraction procedure, which facilitated an efficient analysis. The extraction protocol resulted in an almost complete analyte recovery. Almost no matrix effects were observed among various plasma batches, moreover the matrix did not interfere with the analysis of LSD or O-H-LSD. The quantification of both analytes was accurate and precise within the chosen calibration range and compatible with observed levels in humans dosed with LSD. Overall, the current bioanalytical method is an important tool to further progress the development of LSD as a therapeutic agent.

Throughout this application, various publications, including if available United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Berg T, Jrgenrud B, & Strand D H (2013). Determination of buprenorphine, fentanyl and LSD in whole blood by UPLC-MS-MS. Journal of Analytical Toxicology 37: 159-165.
2. Bershad A K, Schepers S T, Bremmer M P, Lee R, & de Wit H (2019). Acute Subjective and Behavioral Effects of Microdoses of Lysergic Acid Diethylamide in Healthy Human Volunteers. Biological Psychiatry 86: 792-800.
3. Bogusz M J, Maier R D, Krüger K D, & Kohls U (1998). Determination of common drugs of abuse in body fluids using one isolation procedure and liquid chromatography-atmospheric-pressure chemical-ionization mass spectrometry. Journal of Analytical Toxicology 22: 549-558.
4. Burnley B T, & George S (2003). The development and application of a gas chromatography-mass spectrometric (GC-MS) assay to determine the presence of 2-oxo-3-hydroxy-LSD in urine. Journal of Analytical Toxicology 27: 249-252.
5. Cai J, & Henion J (1996). On-line immunoaffinity extraction-coupled column capillary liquid chromatography/tandem mass spectrometry: Trace analysis of LSD analogs and metabolites in human urine. Analytical Chemistry 68: 72-78.
6. Canezin J, Cailleux A, Turcant A, Le Bouil A, Harry P, & Allain P (2001). Determination of LSD and its metabolites in human biological fluids by high-performance liquid chromatography with electrospray tandem mass spectrometry. Journal of Chromatography B: Biomedical Sciences and Applications 765: 15-27.
7. Caspar A T, Kollas A B, Maurer H H, & Meyer M R (2018). Development of a quantitative approach in blood plasma for low-dosed hallucinogens and opioids using LC-high resolution mass spectrometry. Talanta 176: 635-645.
8. Chung A, Hudson J, & McKay G (2009). Validated ultra-performance liquid chromatography-tandem mass spectrometry method for analyzing LSD, iso-LSD, nor-LSD, and O-H-LSD in blood and urine. Journal of Analytical Toxicology 33: 253-259.
9. Cui M, McCooeye M A, Fraser C, & Mester Z (2005). Quantitation of lysergic acid diethylamide in urine using atmospheric pressure matrix-assisted laser desorption/ionization ion trap mass spectrometry. Analytical Chemistry 76: 7143-7148.
10. Dolder P C, Liechti M E, & Rentsch K M (2014). Development and validation of a rapid turboflow LC-MS/MS method for the quantification of LSD and 2-oxo-3-hydroxy LSD in serum and urine samples of emergency toxicological cases. Analytical and Bioanalytical Chemistry 407: 1577-1584.
11. Dolder P C, Liechti M E, & Rentsch K M (2018). Development and validation of an LC-MS/MS method to quantify lysergic acid diethylamide (LSD), iso-LSD, 2-oxo-3-hydroxy-LSD, and nor-LSD and identify novel metabolites in plasma samples in a controlled clinical trial. Journal of Clinical Laboratory Analysis 32: 12-15.
12. Dolder P C, Schmid Y, Haschke M, Rentsch K M, & Liechti M E (2015). Pharmacokinetics and concentration-effect relationship of oral LSD in humans. Int J Neuropsychopharmacol 19: pyv072.
13. Dolder P C, Schmid Y, Steuer A E, Kraemer T, Rentsch K M, Hammann F, & Liechti M E (2017). Pharmacokinetics and pharmacodynamics of lysergic acid diethylamide in healthy subjects. Clinical Pharmacokinetics 56: 1219-1230.
14. EMA (2011). Guideline on bioanalytical method validation. European Medicines Agency (https://www.ema.europa.eu/en/bioanalytical-method-validation)
15. Family N, Maillet E L, Williams L T J, Krediet E, Carhart-Harris R L, Williams T M, Nichols C D, Goble D J, & Raz S (2020). Safety, tolerability, pharmacokinetics, and pharmacodynamics of low dose lysergic acid diethylamide (LSD) in healthy older volunteers. Psychopharmacology 237: 841-853.
16. Favretto D, Frison G, Maietti S, & Ferrara S D (2007). LC-ESI-MS/MS on an ion trap for the determination of LSD, iso-LSD, nor-LSD and 2-oxo-3-hydroxy-LSD in blood, urine and vitreous humor. International Journal of Legal Medicine 121: 259-265.
17. FDA (2018). Bioanalytical Method Validation Guidance for Industry. U.S. Food and drug administration (https://www.fda.gov/regulatory-information/search-fda-guidance-documents/bioanalytical-method-validation-guidance-industry)
18. Fisichella M, Odoardi S, & Strano-Rossi S (2015). High-throughput dispersive liquid/liquid microextraction (DLLME) method for the rapid determination of drugs of abuse, benzodiazepines and other psychotropic medications in blood samples by liquid chromatography-tandem mass spectrometry (LC-MS/MS) and app. Microchemical Journal 123: 33-41.
19. Francom P, Andrenyak D, Lim H K, Bridges R R, Jones R T, & Foltz R L (1988). Determination of lsd in urine by capillary column gas chromatography and electron impact mass spectrometry. Journal of Analytical Toxicology 12: 1-8.
20. Gasser P, Holstein D, Michel Y, Doblin R, Yazar-Klosinski B, Passie T, & Brenneisen R (2014). Safety and efficacy of lysergic acid diethylamide-assisted psychotherapy for anxiety associated with life-threatening diseases. Journal of Nervous and Mental Disease 202: 513-520.
21. Grumann C, Henkel K, Stratford A, Hermanns-Clausen M, Passie T, Brandt S D, & Auwärter V (2019). Validation of an LC-MS/MS method for the quantitative analysis of 1P-LSD and its tentative metabolite LSD in fortified urine and serum samples including stability tests for 1P-LSD under different storage conditions. Journal of Pharmaceutical and Biomedical Analysis 174: 270-276.
22. Hoja H, Marquet P, Verneuil B, Lotfi H, Dupuy J L, & Lachâtre G (1997). Determination of LSD and N-demethyl-LSD in urine by liquid chromatography coupled to electrospray ionization mass spectrometry. Journal of Chromatography B: Biomedical Applications 692: 329-335.
23. Holze F, Duthaler U, Vizeli P, Muller F, Borgwardt S, & Liechti M E (2019). Pharmacokinetics and subjective effects of a novel oral LSD formulation in healthy subjects. British Journal of Clinical Pharmacology 85: 1474-1483.
24. Holze F, Liechti M E, Hutten N, Mason N L, Dolder P C, Theunissen E L, Duthaler U, Feilding A, Ramaekers J G, & Kuypers K P C (2021a). Pharmacokinetics and pharmacodynamics of lysergic acid diethylamide microdoses in healthy participants. Clinical and Pharmacological Therapeutics 109: 658-666.
25. Holze F, Vizeli P, Ley L, Müller F, Dolder P, Stocker M, Duthaler U, Varghese N, Eckert A, Borgwardt S, & Liechti M E (2021b). Acute dose-dependent effects of lysergic acid diethylamide in a double-blind placebo-controlled study in healthy subjects. Neuropsychopharmacology 46: 537-544.
26. Horn C K, Klette K L, & Stout P R (2003). LC-MS analysis of 2-oxo-3-hydroxy LSD from urine using a Speedisk® positive-pressure processor with Cerex® Polychrom™ CLIN II columns. Journal of Analytical Toxicology 27: 459-463.
27. Hutten N, Mason N L, Dolder P, Theunissen E L, Holze F, Liechti M E, Varghese N, Eckert A, Feilding A, Ramaekers J G, & Kuypers K P (2020). Low dose LSD acutely increases BDNF blood plasma levels in healthy volunteers. ACS Pharmacolgial Translational Science 31:461-466.
28. Hutten N, Mason N L, Dolder P C, & Kuypers K P C (2019). Motives and Side-Effects of Microdosing With Psychedelics Among Users. Internatonal Journal of Neuropsychopharmacology 22: 426-434.
29. Jang M, Kim J, Han I, & Yang W (2015). Simultaneous determination of LSD and 2-oxo-3-hydroxy LSD in hair and urine by LC-MS/MS and its application to forensic cases. Journal of Pharmaceutical and Biomedical Analysis 115: 138-143.
30. Johansen S S, & Jensen J L (2005). Liquid chromatography-tandem mass spectrometry determination of LSD, ISO-LSD, and the main metabolite 2-oxo-3-hydroxy-LSD in forensic samples and application in a forensic case. Journal of Chromatography B: Analytical Technologies in the Biomedical and Life Sciences 825: 21-28.
31. Klette K L, Horn C K, Stout P R, & Anderson C J (2002). LC-MS analysis of human urine specimens for 2-Oxo-3-hydroxy LSD: Method validation for potential interferants and stability study of 2-Oxo-3-hydroxy LSD under various storage conditions. Journal of Analytical Toxicology 26: 193-200.
32. Krebs T S, & Johansen P O (2013). Over 30 million psychedelic users in the United States. F1000Res 2: 98.
33. Kuypers K P, Ng L, Erritzoe D, Knudsen G M, Nichols C D, Nichols D E, Pani L, Soula A, & Nutt D (2019). Microdosing psychedelics: more questions than answers? An overview and suggestions for future research. Journal of Psychopharmacology 33: 1039-1057.
34. Kuypers K P C (2020). The therapeutic potential of microdosing psychedelics in depression. Therapeutic Advances in Psychopharmacology 10: 2045125320950567.
35. Libong D, Bouchonnet S, & Ricordel I (2003). A selective and sensitive method for quantitation of lysergic acid diethylamide (LSD) in whole blood by gas chromatography-ion trap tandem mass spectrometry. Journal of Analytical Toxicology 27: 24-29.
36. Liechti M E (2017). Modern Clinical Research on LSD. Neuropsychopharmacology 42: 2114-2127.
37. Lim H K, Andrenyak D, Francom P, Foltz R L, & Jones R T (1988). Quantification of LSD and N-Demethyl-LSD in Urine by Gas Chromatography/Resonance Electron Capture Ionization Mass Spectrometry. Analytical Chemistry 60: 1420-1425.
38. Martin R, Schärenkamp J, Gasse A, Pfeiffer H, & Köhler H (2013). Determination of psilocin, bufotenine, LSD and its metabolites in serum, plasma and urine by SPE-LC-MS/MS. International Journal of Legal Medicine 127: 593-601.
39. Nelson C C, & Foltz R L (1992). Determination of Lysergic Acid Diethylamide (LSD), Iso-LSD, and /V-Demethyl-LSD in Body Fluids by Gas Chromatography/Tandem Mass Spectrometry. Analytical Chemistry 64: 1578-1585.
40. Musshoff, F. and T. Daldrup (1997). "Gas chromatographic/mass spectrometric determination of lysergic acid diethylamide (LSD) in serum samples." Forensic Science International 88: 133-140.
41. Papac D I, & Foltz R L (1990). Measurement of lysergic acid diethylamide (lsd) in human plasma by gas chromatography/negative ion chemical ionization mass spectrometry. Journal of Analytical Toxicology 14: 189-190.
42. Paul B D, Mitchell J M, Burbage R, Moy M, & Sroka R (1990). Gas chromatographic-electron-impact mass fragmentometric determination of lysergic acid diethylamide in urine. Journal of Chromatography B: Biomedical Sciences and Applications 529: 103-112.
43. Paulke A, Kremer C, Wunder C, & Toennes S W (2012). Analysis of lysergic acid amide in human serum and urine after ingestion of Argyreia nervosa seeds. Analytical and Bioanalytical Chemistry 404: 531-538.
44. Pietsch J, Schulz K, Körner B, Trauer H, Dreßler J, & Gey M (2004). Alternative method for forensic determination of lysergic acid diethylamide and related compounds in body fluids by liquid-liquid extraction and HPLC with fluorescence detection. Chromatographia 60: 89-92.
45. Poch G K, Klette K L, & Anderson C (2000). The quantitation of 2-oxo-3-hydroxy lysergic acid diethylamide (O-H-LSD) in human urine specimens, a metabolite of LSD: Comparative analysis using liquid chromatography-selected ion monitoring mass spectrometry and liquid chromatography-ion trap mass spec. Journal of Analytical Toxicology 24: 170-179.
46. Ramaekers J G, Hutten N, Mason N L, Dolder P, Theunissen E L, Holze F, Liechti M E, Feilding A, & Kuypers K P (2021). A low dose of lysergic acid diethylamide decreases pain perception in healthy volunteers. Journal of Psychopharmacology 35:398-405.
47. Reuschel S A, Percey S E, Liu S, Eades D M, & Foltz R L (1999). Quantitative determination of LSD and a major metabolite, 2-oxo-3-hydroxy-LSD, in human urine by solid-phase extraction and gas chromatography-tandem mass spectrometry. Journal of Analytical Toxicology 23: 306-312.
48. Rule G S, & Henion J D (1992). Determination of drugs from urine by on-line immunoaffinity chromatography-high-performance liquid chromatography-mass spectrometry. Journal of Chromatography B: Biomedical Sciences and Applications 582: 103-112.
49. Sklerov J H, Kalasinsky K S, & Ehorn C A (1999). Detection of lysergic acid diethylamide (LSD) in urine by gas chromatography-ion trap tandem mass spectrometry. Journal of Analytical Toxicology 23: 474-478.
50. Sklerov J H, Magluilo J, Jr., Shannon K K, & Smith M L (2000). Liquid chromatography-electrospray ionization mass spectrometry for the detection of lysergide and a major metabolite 2-oxo-3-hydroxy-LSD, in urine and blood. Journal of Analytical Toxicology 24: 543-549.
51. Steuer A E, Poetzsch M, Stock L, Eisenbeiss L, Schmid Y, Liechti M E, & Kraemer T (2017). Development and validation of an ultra-fast and sensitive microflow liquid chromatography-tandem mass spectrometry (MFLC-MS/

MS) method for quantification of LSD and its metabolites in plasma and application to a controlled LSD administration study in huma. Drug Testing and Analysis 9: 788-797.
52. White S A, Catterick T, Harrison M E, Johnston D E, Reed G D, & Webb K S (1997). Determination of lysergide in urine by high-performance liquid chromatography combined with electrospray ionisation mass spectrometry. Journal of Chromatography B: Biomedical Applications 689: 335-340.
53. Yanakieva S, Polychroni N, Family N, Williams L T J, Luke D P, & Terhune D B (2019). The effects of microdose LSD on time perception: a randomised, double-blind, placebo-controlled trial. Psychopharmacology 236: 1159-1170.

What is claimed is:

1. A method of treating and monitoring an individual taking LSD, including the steps of:
   administering a microdose of LSD, a prodrug of LSD, or an analog of LSD to the individual;
   monitoring the individual by obtaining a sample from an individual of about 300 µL of plasma and measuring and identifying analytes in the sample by performing a LC-MS/MS analysis by aliquoting about 50 µL of the sample and mixing with internal standard working solution of acetonitrile, precipitating plasma proteins in the sample with acetonitrile, centrifuging the aliquot, injecting the aliquot into an LC-MS/MS system, diluting the injected aliquot online via a T-union installed in front of a pH resistant analytical column, and detecting LSD and O-H-LSD by multiple reaction monitoring in positive and negative electrospray ionization, wherein analysis of the sample can be run in about 4 minutes, and wherein analysis can quantify 0.5 pg LSD; and
   adjusting the microdose based on the amount of LSD measured and identified in the LC-MS/MS analysis.

2. The method of claim 1, wherein the individual is not responding to the microdose.

3. The method of claim 1, further including the step of identifying if the individual is a slow or rapid metabolizer.

4. The method of claim 1, further including the step of diagnosing an intoxication.

5. The method of claim 1, wherein the microdose is 5 to 200 µg.

* * * * *